(12) United States Patent
Pfaltz et al.

(10) Patent No.: US 6,498,256 B2
(45) Date of Patent: Dec. 24, 2002

(54) PHOSPHINITE-OXAZOLINES AND METAL COMPLEXES THEREOF

(75) Inventors: Andreas Pfaltz, Binningen (CH); Joerg R. Blankenstein, Pulheim (DE); Frederik Menges, Basel (CH)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 09/955,981

(22) Filed: Sep. 20, 2001

(65) Prior Publication Data

US 2002/0062027 A1 May 23, 2002

(30) Foreign Application Priority Data

Sep. 21, 2000 (CH) ................................ 1833/00
Jun. 26, 2001 (CH) ................................ 1177/01

(51) Int. Cl.[7] .......................................... C07D 263/10
(52) U.S. Cl. ...................... 548/112; 548/239; 548/119
(58) Field of Search ............................... 548/112, 119, 548/239, 237

(56) References Cited

U.S. PATENT DOCUMENTS 6,229,019 B1 * 5/2001 Nakamoto et al. .......... 548/110

FOREIGN PATENT DOCUMENTS

| DE | 42 43 030 | 6/1994 |
| WO | 00/61589 | 10/2000 |

OTHER PUBLICATIONS

Helmchen, G., et al. "Phosphinooxazolines—A New Class of Versatile, Modular P,N–Ligands for Asymmetric Catalysis", Accounts of Chemical Research, vol. 33, No. 6, pp. 336–345 (2000).

Jones, G., et al. "Simple phosphinite–oxazoline ligands for asymmetric catalysis", Tetrahedron Letters, vol. 42 (2001), pp. 5553–5555.

Allen, J.V., et al. "Enantiomericaly Pure Oxazolines Tethered to Alcohols. Preparation and Use in Asymmetric Catalysis", Tetrahedron: Asymmetry, vol. 5, No. 2 (1994), pp. 277–282.

Hansen, J.F., et al. "Preparation and Alkylation of a New Chiral Oxazoline from L–Serine", J. Org. Chem., vol. 41, No. 19 (1976), pp. 3219–3220.

Novachek, K.A., et al. "A Convenient Procedure for the Reduction of S–(+)–Silyl Serine Methyl Ester to Chiral Serinol Derivatives", Tetrahedron Letters, vol. 37, No. 11 (1996), pp. 1743–1746.

* cited by examiner

Primary Examiner—Floyd D. Higel
Assistant Examiner—Kamal Saeed
(74) Attorney, Agent, or Firm—Wenderoth, Lind & Ponack, L.L.P.

(57) ABSTRACT

Compounds of formulae I and Ia,

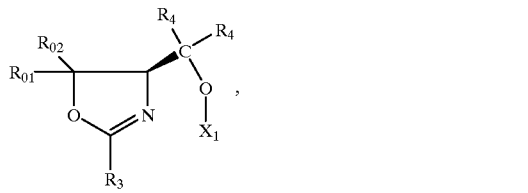

(I)

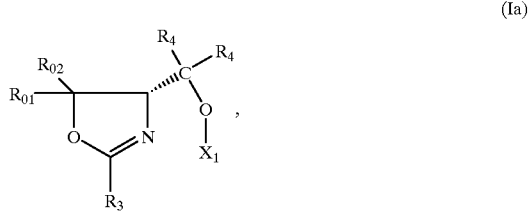

(Ia)

wherein $X_1$ is secondary phosphino; $R_3$ is hydrogen, a hydrocarbon radical having from 1 to 20 carbon atoms, a heterohydrocarbon radical, bonded via a carbon atom, having from 2 to 20 atoms and at least one hetero atom selected from the group O, S and NR, or ferrocenyl; R is H or $C_1$–$C_4$alkyl; each $R_4$ individually or both $R_4$ together are a hydrocarbon radical having from 1 to 20 carbon atoms; and $R_{01}$ and $R_{02}$ are each independently of the other a hydrogen atom or a hydrocarbon radical having from 1 to 20 carbon atoms, are chiral ligands for metal complexes with metals of sub-groups I and VII, which are catalysts for asymmetric addition reactions, for example of hydrogen, to prochiral unsaturated organic compounds.

12 Claims, No Drawings

PHOSPHINITE-OXAZOLINES AND METAL COMPLEXES THEREOF

The present invention relates to chiral phosphinitemothyl-oxazolines; to a process for the preparation thereof; to intermediates used in the preparation thereof; to metal complexes with metals selected from sub-groups I and VII of the Periodic Table of the Elements (d-10 and d-8 metals, referred to as TM8 metals hereinbelow) and phosphinitomethyl-oxazolines as ligands; to a process for asymmetric synthesis by means of an addition reaction between hydrogen, borohydrides or silanes and a carbon-carbon or carbon-hetero atom multiple bond in prochiral organic compounds or by means of an addition reaction between C-nucleophiles or amines and allylic compounds, especially for asymmetric hydrogenation of carbon-carbon or carbon-hetero atom multiple bonds with hydrogen, in the presence of catalytic amounts of the metal complexes; and to the use of the metal complexes as catalysts for asymmetric synthesis by means of an addition reaction between hydrogen, borohydrides or silanes and a carbon-carbon or carbon-hetero atom multiple bond in prochiral organic compounds or by means of an addition reaction between C-nucleophiles or amines and allylic compounds, especially for asymmetric hydrogenation of carbon-carbon or carbon-hetero atom multiple bonds with hydrogen.

G. Helmchen and A. Pfaltz in Accounts of Chemical Research, Volume 33, Number 6, pages 336 to 345 (2000) describe chiral phosphinophenyl-oxazolines as P,N ligands for asymmetric catalysts that are used inter alia in the enantioselective addition of nucleophiles to carbon-carbon double bonds. The oxazoline ring is substituted with bulky groups in the α-position to the nitrogen atom to form an asymmetric centre (carbon atom).

It has been found, surprisingly, that it is possible to prepare in simple manner P,N ligands that contain a phosphinitemethyl group in the α-position to the nitrogen atom to form an asymmetric centre (carbon atom), which phosphinitemethyl group serves at the same time as a chelating group. Those substituted oxazolines form with TM8 metals chiral complexes that are excellent catalysts for the enantioselective addition of hydrogen, borohydrides or silanes to a carbon-carbon or carbon-hetero atom multiple bond in prochiral organic compounds or of C-nucleophiles or amines to allylic compounds or for the enantioselective coupling of aryl or alkenyl triflates to olefins (Heck reaction). Especially in the enantio-selective hydrogenation of prochiral olefins catalysed with Ir complexes, particularly high optical yields are observed. In addition, the phosphinite groups in the ligands exhibit a surprisingly high stability towards hydrolysis. The starting materials for the preparation of the ligands are simple, in some cases commercially available organic molecules that can be combined with one another in a variety of ways, so that the steric and electronic properties of the ligands in respect of catalytic activity and steric selectivity can be adapted to the substrates to be reacted in an outstanding manner.

The invention relates to compounds of formulae I and Ia,

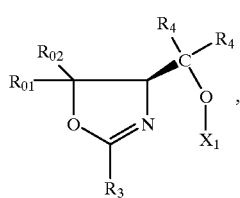

(I)

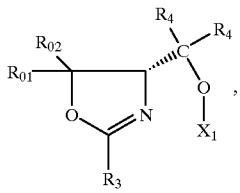

(Ia)

wherein

X$_1$ is secondary phosphino;

R$_3$ is hydrogen, a hydrocarbon radical having from 1 to 20 carbon atoms, a heterohydro-carbon radical, bonded via a carbon atom, having from 2 to 20 atoms and at least one hetero atom selected from the group OS and NR, or ferrocenyl;

R is H or C$_1$–C$_4$alkyl;

each R$_4$ individually or both R$_4$ together are a hydrocarbon radical having from 1 to 20 carbon atoms; and R$_{01}$ and R$_{02}$ are each independently of the other a hydrogen atom or a hydrocarbon radical having from 1 to 20 carbon atoms.

The phosphine group X$_1$ may contain two identical or two different hydrocarbon radicals or the two hydrocarbon radicals may form with the P atom a 3- to 8-membered ring. Preferably the phosphine group contains two identical hydrocarbon radicals. The hydrocarbon radicals may be unsubstituted or substituted and they may contain from 1 to 22, preferably from 1 to 12, carbon atoms. Of the compounds of formulae I and Ia special preference is given to those wherein the phosphine group contains two identical or different radicals selected from the group: linear or branched C$_1$–C$_{12}$alkyl; C$_5$–C$_{12}$cycloalkyl or C$_5$–C$_{12}$cycloalkyl-CH$_2$— unsubstituted or substituted by C$_1$–C$_6$alkyl or by C$_1$–C$_6$alkoxy; phenyl or benzyl; and phenyl or benzyl substituted by halogen (for example F, Cl and Br), C$_1$–C$_6$alkyl, C$_1$–C$_6$haloalkyl (for example trifluoromethyl), C$_1$–C$_6$alkoxy, C$_1$–C$_6$haloalkoxy (for example trifluoromethoxy), (C$_6$H$_5$)$_3$Si, (C$_1$–C$_{12}$alkyl)$_3$Si, secondary amino or by —CO$_2$—C$_1$–C$_6$alkyl (for example —CO$_2$CH$_3$).

The two radicals in the phosphine group may together also be dimethylene, trimethylene, tetramethylene or pentamethylene unsubstituted or substituted by halogen, C$_1$–C$_6$alkyl or by C$_1$–C$_6$alkoxy. The substituents are preferably bonded in the two ortho positions to the P atom.

The phosphine groups may also be those of formulae

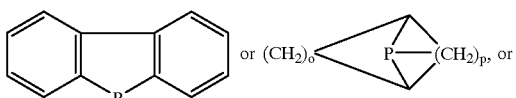

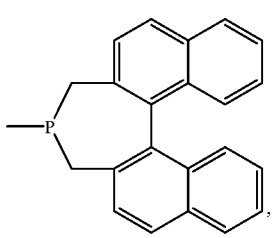

wherein o and p are each independently of the other an integer from 2 to 10, and the sum of o+p is from 4 to 12, preferably from 5 to 8, and the phenyl rings are unsubstituted or substituted by $C_1$–$C_4$alkyl and $C_1$–$C_4$alkoxy. Examples are [3.3.1]- and [4.2.1]-phobyl of the formulae

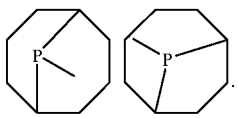

Examples of secondary phosphine groups in which the two hydrocarbon radicals form with the P atom a 3- to 8-membered ring are especially those of the formula

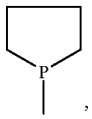

which may be substituted in one or both ortho positions and optionally the meta positions to the P atom by $C_1$–$C_4$alkyl and/or by $C_1$–$C_4$alkoxy.

Examples of P substituents as alkyl, which preferably contains from 1 to 6 carbon atoms, are methyl, ethyl, n-propyl, isopropyl, n-butyl, isobutyl, tert-butyl, and the isomers of pentyl and hexyl. Examples of P substituents as unsubstituted or alkyl-substituted cycloalkyl are cyclopentyl, cyclohexyl, methyl- and ethyl-cyclohexyl and dimethylcyclohexyl. Examples of P substituents as phenyl and benzyl substituted by alkyl, alkoxy, haloalkyl and/or by haloalkoxy are methylphenyl, dimethylphenyl, trimethylphenyl, ethylphenyl, methylbenzyl, methoxyphenyl, dimethoxyphenyl, trifluoromethylphenyl, bis-trifluoromethylphenyl, tris-trifluoromethylphenyl, trifluoromethoxyphenyl and bis-trifluoromethoxyphenyl.

Preferred phosphine groups $X_1$ are those which contain identical or different, preferably identical, radicals selected from the group $C_1$–$C_6$alkyl; cyclopentyl or cyclohexyl unsubstituted or substituted by from 1 to 3 $C_1$–$C_4$alkyl or $C_1$–$C_4$alkoxy substituents; benzyl and especially phenyl, which are unsubstituted or substituted by from 1 to 3 $C_1$–$C_4$alkyl, $C_1$–$C_4$alkoxy, F, Cl, $C_1$–$C_4$fluoroalkyl or $C_1$–$C_4$fluoroalkoxy substituents.

In the compounds of formula I, $X_1$ is preferably the group —$PR_1R_2$ wherein $R_1$ and $R_2$ are each independently of the other a hydrocarbon radical having from 1 to 20 carbon atoms, which is unsubstituted or substituted by halogen, $C_1$–$C_6$alkyl, $C_1$–$C_6$haloalkyl, $C_1$–$C_6$alkoxy, $C_1$–$C_6$haloalkoxy, $(C_6H_5)_3Si$, $(C_1$–$C_{12}alkyl)_3Si$ or by —$CO_2$—$C_1$–$C_6$alkyl; or wherein $R_1$ and $R_2$ together are dimethylene, trimethylene, tetramethylene or pentamethylene unsubstituted or substituted by $C_1$–$C_4$alkyl and/or by $C_1$–$C_4$alkoxy.

$R_1$ and $R_2$ are preferably identical or different, especially identical, radicals selected from the group: branched $C_3$–$C_6$alkyl; cyclopentyl or cyclohexyl unsubstituted or substituted by from one to three $C_1$–$C_4$alkyl or $C_1$–$C_4$alkoxy substituents; benzyl unsubstituted or substituted by from one to three $C_1$–$C_4$alkyl or $C_1$–$C_4$alkoxy substituents, and especially phenyl unsubstituted or substituted by from one to three $C_1$–$C_4$alkyl, $C_1$–$C_4$alkoxy, —$NH_2$, OH, F, Cl, $C_1$–$C_4$fluoroalkyl or $C_1$–$C_4$fluoroalkoxy substituents.

$R_1$ and $R_2$ are more especially identical or different, especially identical, radicals selected from the group: phenyl unsubstituted or substituted by from one to three $C_1$–$C_4$alkyl, $C_1$–$C_4$alkoxy or $C_1$–$C_4$fluoroalkyl substituents.

The radicals $R_3$ and $R_4$ may be unsubstituted or substituted, for example by $C_1$–$C_6$alkyl, $C_1$–$C_6$alkoxy, cyclohexyl, $C_6$–$C_{10}$aryl, $C_7$–$C_{12}$aralkyl, $C_1$–$C_4$alkyl-$C_6$–$C_{10}$aryl, $C_1$$C_4$alkoxy-$C_6$–$C_{10}$aryl, $C_1$–$C_4$alkyl-$C_7$–$C_{12}$aralkyl, $C_1$–$C_4$alkoxy-$C_7$–$C_{12}$aralkyl, —CO—$OR_5$, —CO—$NR_6R_7$ or by —$NR_6R_7$, wherein $R_5$ is H, an alkali metal, $C_1$–$C_6$alkyl, cyclohexyl, phenyl or benzyl, and $R_6$ and $R_7$ are each independently of the other hydrogen, $C_1$–$C_6$alkyl, cyclohexyl, phenyl or benzyl, or $R_6$ and $R_7$ together are tetramethylene, pentamethylene or 3-oxapentylene.

The hydrocarbon radical $R_3$ contains preferably from 1 to 16, more especially from 1 to 12, carbon atoms. The hydrocarbon radical $R_3$ may be $C_1$–$C_{18}$alkyl, preferably $C_1$–$C_{12}$alkyl and more especially $C_1$–$C_8$alkyl; $C_3$–$C_{12}$cycloalkyl, preferably $C_4$–$C_8$cycloalkyl and more especially $C_5$–$C_6$cycloalkyl; or $C_6C_{16}$aryl and preferably $C_6$–$C_{12}$aryl.

When $R_3$ is alkyl, it is preferably branched $C_3$–$C_8$alkyl. Examples of alkyl are methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl and eicosyl. Preferred alkyl is isopropyl, isobutyl, tert-butyl, isopentyl, isohexyl and 1,1,2,2-tetramethylethyl.

When $R_3$ is cycloalkyl, it may be, for example, cyclopropyl, cyclobutyl, cyclopentyl, cyclohexyl, cycloheptyl, cyclooctyl, cyclodecyl or cyclododecyl.

When $R_3$ is aryl, it may be, for example, phenyl, naphthyl, anthracenyl, phenanthryl, biphenyl or ferrocenyl.

The heterohydrocarbon radical $R_3$ contains preferably a total of from 1 to 16, more especially a total of from 1 to 12, atoms and from 1 to 3 hetero atoms selected from the group O, S and NR. The heterohydrocarbon radical $R_3$ may be $C_1$–$C_{18}$heteroalkyl, preferably $C_1$–$C_2$heteroalkyl and more especially $C_1$–$C_8$heteroalkyl; $C_3$–$C_{12}$heterocycloalkyl, preferably $C_4$–$C_8$heterocycloalkyl and more especially $C_4$–$C_5$heterocycloalkyl; or $C_4$–$C_{16}$heteroaryl and preferably $C_4$–$C_{11}$heteroaryl.

When $R_3$ is ferrocenyl, the ferrocenyl is unsubstituted or substituted by at least one $C_1$–$C_4$alkyl, $C_1$–$C_4$alkoxy, trimethylsilyl or halogen substituent, for example methyl, ethyl, n- or iso-propyl, butyl, methoxy, ethoxy, F, Cl or Br.

When $R_3$ is alkyl, it is preferably $C_1$–$C_8$alkyl. Examples of heteroalkyl are methoxymethyl, methoxyethyl, ethoxymethyl, ethoxyethyl, ethoxypropyl, isopropoxymethyl, isopropoxyethyl, isobutoxyethyl, tert-butoxyethyl, methylthioethyl and dimethylaminoethyl.

When $R_3$ is heterocycloalkyl, it may be, for example, oxetanyl, tetrahydrofuranyl, oxacyclohexyl, dioxanyl, pyrrolidinyl or N-methylazacyclohexyl.

When $R_3$ is heteroaryl, it may be, for example, furanyl, thiophenyl, pyrrolyl, pyridinyl, pyrimidinyl, indolyl, quinolinyl or quinoxalinyl.

In a preferred sub-group, $R_3$ is a hydrocarbon radical selected from the group: branched $C_3$–$C_{12}$alkyl, $C_5$–$C_6$cycloalkyl, ferrocenyl and $C_6$–$C_{12}$aryl, the cyclic radicals being unsubstituted or substituted by halogen (F, Cl, Br), $C_1$–$C_4$alkyl or by $C_1$–$C_4$alkoxy.

$R_4$ as a hydrocarbon radical contains preferably from 1 to 16, especially from 1 to 12, more especially from 1 to 8, carbon atoms. The hydrocarbon radical $R_4$ may be $C_1$–$C_{18}$alkyl, preferably $C_1$–$C_{12}$alkyl and more especially $C_1$–$C_8$alkyl; $C_3$–$C_{12}$cycloalkyl, preferably $C_4$–$C_8$cycloalkyl and more especially $C_5$–$C_6$cycloalkyl; $C_6$–$C_{16}$aryl and preferably $C_6$–$C_{12}$aryl, or $C_7$–$C_{16}$aralkyl and preferably $C_7$–$C_{12}$aralkyl.

When the two $R_4$ are a hydrocarbon radical, that radical is alkylene, which preferably contains from 3 to 7, more especially from 4 to 6, carbon atoms. Examples are 1,3-propylene, 1,3- or 1,4-butylene, 1,3-, 1,4- or 1,5-pentylene and 1,3-, 1,4-, 1,5-, 2,5-, 2,6- or 1,4-hexylene.

The embodiments and preferences given for $R_3$ apply to $R_4$ in respect of alkyl, cycloalkyl and aryl. When $R_4$ is aralkyl, it is preferably benzyl or naphthylmethyl, which are unsubstituted or substituted by halogen (F, Cl, Br), $C_1$–$C_4$alkyl or by $C_1$–$C_4$alkoxy.

In a preferred sub-group, $R_4$ is a hydrocarbon radical selected from the group: branched $C_3$–$C_{12}$alkyl, $C_5$–$C_6$cycloalkyl, $C_6$–$C_{12}$aryl and $C_7$–$C_{12}$aralkyl, the cyclic radicals being unsubstituted or substituted by halogen (F, Cl, Br), $C_1$–$C_4$alkyl, $C_1$–$C_4$haloalkyl (for example trifluoromethyl) or by $C_1$–$C_4$alkoxy.

The embodiments and preferences given for $R_4$ apply independently to $R_{01}$ and $R_{02}$. When $R_{01}$ and $R_{02}$ are different radicals or one of $R_{01}$ and $R_{02}$ is a hydrogen atom, the compounds of formulae I and Ia contain a further chiral carbon atom. The invention relates also to racemates or diastereoisomers of those compounds. The relative configuration of the diastereoisomers may have a positive influence on the enantioselectivity in addition reactions catalysed according to the invention. $R_{01}$ and $R_{02}$ are preferably each hydrogen. In another preferred group, $R_{01}$ is hydrogen and $R_{02}$ is $C_1$–$C_4$alkyl.

A preferred sub-group of the compounds according to the invention comprises those of formulae Ib and Ic,

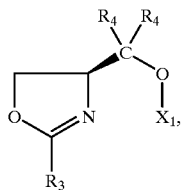
(Ib)

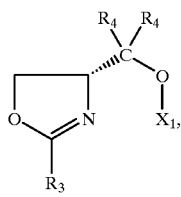
(Ic)

wherein $X_1$ is —$PR_1R_2$, $R_1$ and $R_2$ are identical or different, especially identical, radicals selected from the group: α-branched $C_3$–$C_6$alkyl; $C_5$–$C_7$cycloalkyl unsubstituted or substituted by from one to three $C_1$–$C_4$alkyl or $C_1$–$C_4$alkoxy substituents; phenyl unsubstituted or substituted by from one to three $C_1$–$C_4$alkyl, $C_1$–$C_4$alkoxy or $C_1$–$C_4$fluoroalkyl substituents; and dimethylene, trimethylene, tetramethylene or hexamethylene unsubstituted or substituted by $C_1$–$C_4$alkyl or by $C_1$–$C_4$alkoxy;

$R_3$ is a hydrocarbon radical selected from the group: branched $C_3$–$C_{12}$alkyl, $C_5$–$C_6$cycloalkyl, $C_6$–$C_{12}$aryl and ferrocenyl, the cyclic radicals being unsubstituted or substituted by halogen, $C_1$–$C_4$alkyl, $C_1$–$C_4$haloalkyl or by $C_1$–$C_4$alkoxy; and $R_4$ is a hydrocarbon radical selected from the group: branched $C_3$–$C_{12}$alkyl, $C_5$–$C_6$cycloalkyl, $C_6$–$C_{12}$aryl and $C_7$$C_{12}$aralkyl, the cyclic radicals being unsubstituted or substituted by halogen, $C_1$–$C_4$alkyl or by $C_1$–$C_4$alkoxy.

The compounds of formulae I and Ia can be prepared in a small number of process steps in two different ways, α-amino-β-hydroxycarboxylic acid esters being a fundamental reagent. In a first variant, iminocarboxylic acid esters are cyclised with α-amino-β-hydroxycarboxylic acid esters to form oxazolinecarboxylic acid esters, the ester group is then converted into a tertiary alcohol group, and subsequently the phosphonite is formed. In a second variant, a carboxylic acid or a carboxylic acid derivative is reacted with an α-amino-β-hydroxycarboxylic acid ester, the ester group is then converted into a tertiary alcohol group, cyclisation to the oxazoline is carried out and subsequently the phosphonite is formed.

The invention relates also to a process for the preparation of compounds of formulae I and Ia,

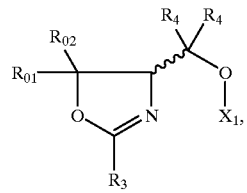
(I and Ia)

wherein $R_{01}$, $R_{02}$, $R_3$, $R_4$ and $X_1$ are as defined above, and ~ denotes the R- or S-form, in which process either a1) a compound of formula II

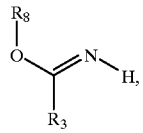
(II)

or a salt thereof, wherein $R_3$ is as defined above and $R_8$ is $C_1$–$C_4$alkyl, is reacted with at least an equivalent amount of a compound of formula III,

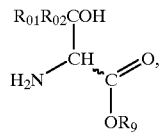
(III)

wherein $R_9$ is $C_1$–$C_4$alkyl, to form a compound of formula IV,

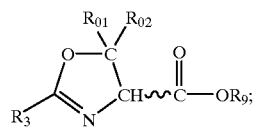
(IV)

a2) the compound of formula IV is reacted with at least 2 equivalents of an organometal compound of formula V or Va $R_4$—$X_2$ (V), $R_4$—$(X_2)_2$ (Va), wherein $R_4$ is as defined above, $X_2$ is an alkali metal or $-Me_1X_3$, $Me_1$ is Mg or Zn, and $X_3$ is Cl, Br or I, to form a compound of formula VI

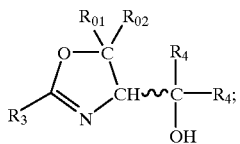 (VI)

and a3) the hydroxyl group in the compound of formula VI is metallated and then reacted with a halophosphine of formula VII, $$X_1-Y_1 \quad \text{(VII)},$$

wherein $X_1$ is as defined above and $Y_1$ is Cl, Br or I, to form a compound of formula Ia or Ib; or b1) a carboxylic acid of formula VIII $$R_3-COOH \quad \text{(VIII)},$$

or a derivative of that carboxylic acid, is reacted with a compound of formula III to form a carboxylic acid amide of formula IX,

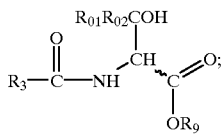 (IX)

b2) the compound of formula IX is reacted with a compound of formula V or Va to form a compound of formula X,

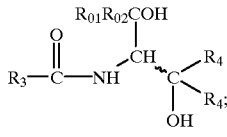 (X)

b3) the compound of formula X is cyclised to form a compound of formula VI; and b4) the hydroxyl group in the compound of formula VI is metallated and then reacted with a halophosphine of formula VII to form a compound of formula Ia or Ib.

The invention relates also to compounds of formula IV wherein $R_{01}$ is a hydrogen atom and $R_{02}$ is a hydrocarbon radical having from 1 to 20 carbon atoms, and $R_3$, $R_4$ and $R_9$ are as defined above.

The invention relates also to compounds of formula VI wherein $R_{01}$ and $R_{02}$ are each independently of the other a hydrogen atom or a hydrocarbon radical having from 1 to 20 carbon atoms, and $R_3$ and $R_4$ are as defined above.

Process Step a1)

The preparation of iminocarboxylic acid esters of formula II is generally known and is described, for example, by L. Weintraub et al. in J. Org. Chem., Volume 33, No. 4, pages 1679 to 1681 (1968). The iminocarboxylic acid esters of formula II are advantageously used in the form of salts, for example tetrafluoroborates. In formula II, $R_8$ may be, for example, methyl, ethyl, n- or iso-propyl or butyl. The reaction can be carried out at temperatures of from 20 to 150° C. It is advantageous to use solvents such as, for example, halogenated hydrocarbons (methylene chloride, trichloromethane or tetrachloroethane). Equivalent amounts of the reactants are generally used. Serinecarboxylic acid esters of formula III are known. $R_9$ may be, for example, methyl, ethyl, n- or iso-propyl or butyl.

Process Step a2)

The reaction of carboxylic acid esters with metal or metal halide hydrocarbons is known per se. When $X_2$ is an alkali metal, it may be Na, K or especially Li. In the group $Me_1X_3$, $Me_1$ may be, for example, Mg or Zn. The reaction is advantageously carried out by adding the compound of formula V at low temperatures, for example from –30 to –80° C., to a solution of the compound of formula IV and then heating the mixture, for example to room temperature. The reaction can then be completed at that temperature or at higher temperatures (up to the boiling temperature of the solvents used). Suitable solvents are especially ethers, such as diethyl ether, dibutyl ether, tetrahydrofuran and dioxane.

Process Step a3)

The metallation of the compound of formula VI to form metal alcoholates can be carried out with alkali metal alkyls and especially lithium alkyl, for example lithium methyl, ethyl, propyl or butyl, or with Grignard reagents, such as methyl-, ethyl-, propyl-, butyl- or benzyl-magnesium halides. It is advantageous to use equivalent amounts or a slight excess of alkali metal alkyls or Grignard reagents. The addition is advantageously made at relatively low temperatures, for example from –20 to –80° C. The presence of tertiary amines, for example trimethyl-, triethyl- or tributyl-amine or tetramethylethylenediamine may be advantageous. Then at room temperature the reaction can be completed, the halophosphine of formula VII added and the reaction ended at that temperature. The reaction is preferably carried out in the presence of inert solvents, for example ethers or hydrocarbons (pentane, hexane, cyclohexane, methylcyclohexane, benzene, toluene or xylene).

Process Step b1)

Suitable derivatives of carboxylic acids are esters, amides and especially halides. The reaction is advantageously carried out in the presence of solvents, for example halogenated hydrocarbons. When carboxylic acids of formula VII are used, the addition of equimolar amounts of tertiary amines is advantageous, for example diisopropylethylamine. The presence of at least equimolar amounts of carbodiimides is also advantageous. In order to suppress racemisation, the carboxylic acids can be converted into activated esters in the presence of metal salts, for example copper salts, with selected alcohols, for example hydroxybenzotriazole. The reaction can be carried out at temperatures of from –30 to 50° C.

Process Step b2)

This reaction can be carried out analogously to Process step a2).

Process Step b3)

The reaction is advantageously carried out in the presence of a solvent, for example halogenated hydrocarbons, and at temperatures of preferably from 50 to 150° C. A tertiary amine, for example triethylamine, and a sulfonic acid halide, such as p-toluenesulfonyl chloride, are added to a solution of the compound of formula X and the mixture is heated to reflux temperature. The reaction mixture is left to react for a period of time, water is added and then the reaction mixture is allowed to react to completion.

Process Step b4)

This reaction can be carried out analogously to Process step a3).

The compounds of formulae Ia and Ib are obtained in good total yields. By selection of the starting compounds it is possible for the compounds according to the invention to be synthesised in a modular manner, the simple starting compounds allowing a large number of substitutions in respect of $R_3$ and $R_4$.

The invention relates also to the intermediates of formulae IV, VI and X obtainable in the process according to the invention.

The compounds of formulae Ia and Ib according to the invention are ligands for metal complexes selected from the group of TM8 metals, especially from the group Ru, Rh and Ir, which are excellent catalysts or catalyst precursors for asymmetric syntheses, for example the asymmetric hydrogenation of prochiral, unsaturated, organic compounds. When prochiral unsaturated organic compounds are used, it is possible to induce a very large excess of optical isomers in the synthesis of organic compounds and to achieve a high chemical conversion in short reaction times. The enantioselectivities and catalyst activities that are achievable are excellent.

The invention relates also to metal complexes of metals selected from the group of TM8 metals with compounds of formulae I and Ia as ligands.

Examples of metals that come into consideration are Cu, Ag, Au, Ni, Co, Rh, Pd, Ir and Pt. Preferred metals are rhodium and iridium and also ruthenium, platinum and palladium.

Especially preferred metals are ruthenium, rhodium and iridium.

The metal complexes may, according to the oxidation state and coordination number of the metal atom, contain further ligands and/or anions. They may also be cationic metal complexes. Such analogous metal complexes and their preparation are frequently described in the literature.

The metal complexes may correspond, for example, to the general formulae XI and XII,

wherein $A_1$ is a compound of formula I or Ia,

L denotes identical or different, monodentate, anionic or non-ionic ligands, or two L denote identical or different, bidentate, anionic or non-ionic ligands;

n is 2, 3 or 4 when L is a monodentate ligand, or n is 1 or 2 when L is a bidentate ligand;

z is 1, 2 or 3;

Me is a metal selected from the group Rh, Ir and Ru; the metal having the oxidation state 0, 1, 2, 3 or 4;

$E^-$ is the anion of an oxyacid or complex acid; and the anionic ligands balance the charge of oxidation states 1, 2, 3 or 4 of the metal.

The preferences and embodiments described above apply to the compounds of formulae I and Ia.

Monodentate non-ionic ligands may be selected, for example, from the group of olefins (for example ethylene, propylene), allyls (allyl, 2-methallyl), solvating solvents (nitriles, linear or cyclic ethers, optionally N-alkylated amides and lactams, amines, phosphines, alcohols, carboxylic acid esters, sulfonic acid esters), nitrogen monoxide and carbon monoxide.

Monodentate anionic ligands may be selected, for example, from the group halide: (F, Cl, Br, I), pseudohalide (cyanide, cyanate, isocyanate) and anions of carboxylic acids, sulfonic acids and phosphonic acids (carbonate, formate, acetate, propionate, methylsulfonate, trifluoromethylsulfonate, phenylsulfonate, tosylate).

Bidentate non-ionic ligands may be selected, for example, from the group of linear or cyclic diolefins (for example hexadiene, cyclooctadiene, norbornadiene), dinitriles (malonic dinitrile), optionally N-alkylated carboxylic acid diamides, diamines, diphosphines, diols, acetonyl acetonates, dicarboxylic acid diesters and disulfonic acid diesters.

Bidentate anionic ligands may be selected, for example, from the group of anions of dicarboxylic acids, disulfonic acids and diphosphonic acids (for example of oxalic acid, malonic acid, succinic acid, maleic acid, methylenedisulfonic acid and methylenediphosphonic acid).

Preferred metal complexes are also those wherein E is $-Cl^-$, $-Br^-$, $-I^-$, $ClO_4^-$, $CF_3SO_3^-$, $CH_3SO_3^-$, $HSO_4^-$, $(CF_3SO_2)_2N^-$, $(CF_3SO_2)_3C^-$, tetraaryl borates, for example $B(phenyl)_4^-$, $B[bis(3,5-trifluoromethyl)phenyl]_4^-$, $B[bis(3,5-dimethyl)phenyl]_4^-$, $B(C_6F_5)_4^-$ and $B(4-methylphenyl)_4^-$, $BF_4^-$, $PF_6^-$, $SbCl_6^-$, $AsF_6^-$ or $SbF_6^-$.

Especially preferred metal complexes, which are particularly suitable for hydrogenations, correspond to formulae XIII and XIV,

wherein $A_1$ is a compound of formula I or Ia;

$Me_2$ is rhodium or iridium;

Y denotes two olefins or a diene;

Z is Cl, Br or I; and $E_1^-$ is the anion of an oxyacid or complex acid.

The embodiments and preferences described above apply to the compounds of formulae I and Ia.

Y as olefin may denote $C_2$–$C_{12}$-, preferably $C_2$–$C_6$- and more especially $C_2$–$C_4$-olefin. Examples are propene, but-1-ene and especially ethylene. The diene may contain from 5 to 12, preferably from 5 to 8, carbon atoms and it may be an open-chain, cyclic or polycyclic diene. The two olefin groups of the diene are preferably bonded by one or two $CH_2$ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y preferably denotes two ethylene or 1,5-hexadiene, 1,5-cyclooctadiene or norbornadiene.

In formula XIII, Z is preferably Cl or Br. Examples of $E_1$ are $BF_4^-$, $ClO_4^-$, $CF_3SO_3^-$, $CH_3SO_3^-$, $HSO_4^-$, $B(phenyl)_4^-$, $B[bis(3,5-trifluoromethyl)phenyl]_4^-$, $PF_6^-$, $SbCl_6^-$, $AsF_6^-$ and $SbF_6^-$.

The metal complexes according to the invention are prepared in accordance with methods known in the literature (see also U.S. Pat. Nos. 5,371,256, 5,446,844, 5,583,241, and E. Jacobsen, A. Pfaltz, H. Yamamoto (Eds.), Comprehensive Asymmetric Catalysis I to III, Springer Verlag, Berlin, 1999, and literature referred to therein).

The metal complexes according to the invention are homogeneous catalysts, or catalyst precursors capable of being activated under the reaction conditions, which can be used for asymmetric addition reactions with prochiral, unsaturated, organic compounds.

The metal complexes can be used, for example, for the asymmetric hydrogenation (addition of hydrogen) of prochiral compounds having carbon-carbon or carbon-hetero atom multiple bonds, especially double bonds. Such hydrogenations with soluble homogeneous metal complexes are described, for example, in Pure and Appl. Chem., Vol. 68, No. 1, pp. 131–138 (1996). Preferred unsaturated compounds to be hydrogenated contain the groups C=C, C=N and/or C=O. For the hydrogenation the use of metal complexes of rhodium and iridium is preferred according to the invention.

The metal complexes according to the invention can also be used as catalysts in the asymmetric hydroboration (addition of borohydrides) of prochiral organic compounds having carbon-carbon double bonds. Such hydroborations are described, for example, by Tamio Hayashi in E. Jacobsen, A. Pfaltz, H. Yamamoto (Eds.), Comprehensive Asymmetric Catalysis I to III, Springer Verlag, Berlin, 1999, pages 351 to 364. Suitable borohydrides are, for example, catechol boranes. The chiral boron compounds can be used in syntheses and/or reacted in a manner known per se to form other chiral organic compounds that are valuable building blocks for the preparation of chiral intermediates or active ingredients. One example of such a reaction is the preparation of 3-hydroxy-tetrahydrofuran (according to DE 198 07 330).

The metal complexes according to the invention can also be used as catalysts in the asymmetric hydrosilylation (addition of silanes) of prochiral organic compounds having carbon-carbon or carbon-hetero atom double bonds. Such hydrosilylations are described, for example, by G. Pioda and A. Togni in Tetrahedron: Asymmetry, 1998, 9, 3093 or by S. Uemura, et al. in Chem. Commun. 1996, 847. Suitable silanes are, for example, trichlorosilane or diphenylsilane. For the hydrosilylation of, for example, C=O and C=N groups it is preferable to use metal complexes of rhodium and iridium. For the hydrosilylation of, for example, C=C groups it is preferable to use metal complexes of palladium. The chiral silyl compounds can be used in syntheses and/or reacted in a manner known per se to form other chiral organic compounds that are valuable building blocks for the preparation of chiral intermediates or active ingredients. Examples of such reactions are hydrolysis to alcohols.

The metal complexes according to the invention can also be used as catalysts for asymmetric allylic substitution reactions (addition of C-nucleophiles to allyl compounds). Such allylations are described, for example, by A. Pfaltz and M. Lautens in E. Jacobsen, A. Pfaltz, H. Yamamoto (Eds.), Comprehensive Asymmetric Catalysis I to III, Springer Verlag, Berlin, 1999, pages 833 to 884. Suitable precursors for allyl compounds are, for example, 1,3-diphenyl-3-acetoxy-1-propene and 3-acetoxy-1-cyclohexene. For that reaction it is preferable to use metal complexes of palladium. The chiral allyl compounds can be used in syntheses for the preparation of chiral intermediates or active ingredients.

The metal complexes according to the invention can also be used as catalysts in asymmetric amination (addition of amines to allyl compounds) or in asymmetric Heck reactions. Such aminations are described, for example, by A. Pfaltz and M. Lautens in E. Jacobsen, A. Pfaltz, H. Yamamoto (Eds.), Comprehensive Asymmetric Catalysis I to III, Springer Verlag, Berlin, 1999, pages 833 to 884, and Heck reactions by O. Loiseleur et al. in Journal of Organometallic Chemistry 576 (1999), pages 16 to 22. Suitable amines, in addition to ammonia, are primary and secondary amines. For the amination of allyl compounds it is preferable to use metal complexes of palladium. The chiral amines can be used in syntheses for the preparation of chiral intermediates or active ingredients.

The invention relates also to the use of the metal complexes according to the invention as homogeneous catalysts in the preparation of chiral organic compounds by asymmetric addition of hydrogen, borohydrides or silanes to a carbon-carbon or carbon-hetero atom multiple bond in prochiral organic compounds or asymmetric addition of C-nucleophiles or amines to allyl compounds.

The invention relates further to a process for the preparation of chiral organic compounds by asymmetric addition of hydrogen, borohydrides or silanes to a carbon-carbon or carbon-hetero atom multiple bond in prochiral organic compounds or asymmetric addition of C-nucleophiles or amines to allyl compounds in the presence of a catalyst, wherein the addition is carried out in the presence of catalytic amounts of at least one metal complex according to the invention.

Preferred prochiral unsaturated compounds to be hydrogenated may contain one or more, identical or different groups C=C, C=N and/or C=O in open-chain or cyclic organic compounds, the groups C=C, C=N and/or C=O being part of a ring system or being exocyclic groups. The prochiral unsaturated compounds may be alkenes, cycloalkenes and heterocycloalkenes, and also open-chain or cyclic ketones, ketimines and ketohydrazones. They may correspond, for example, to formula X, $$R_{07}R_{08}C=D \qquad (XVIII),$$

wherein $R_{07}$ and $R_{08}$ are so selected that the compound is prochiral and are each independently of the other an open-chain or cyclic hydrocarbon radical or heterohydrocarbon radical having hetero atoms selected from the group O, S and N, that contains from 1 to 30, preferably from 1 to 20, carbon atoms;

D is O or a radical of formula C=$R_{09}R_{10}$ or $NR_{11}$;

$R_{09}$ and $R_{10}$ each independently of the other have the same meanings as $R_{07}$ and $R_{08}$, $R_{11}$ is hydrogen, $C_1$–$C_{12}$alkyl, $C_1$–$C_{12}$alkoxy, $C_3$–$C_{12}$cycloalkyl, $C_3$–$C_{12}$cycloalkyl-$C_1$–$C_6$alkyl, $C_3$–$C_{11}$heterocycloalkyl, $C_3$–$C_{11}$heterocycloalkyl-$C_1$–$C_6$alkyl, $C_6$–$C_{14}$aryl, $C_5$–$C_{13}$heteroaryl, $C_7$–$C_{16}$aralkyl or $C_6$–$C_{14}$heteroaralkyl, $R_{07}$ and $R_{08}$ together with the carbon atom to which they are bonded form a hydrocarbon ring or heterohydrocarbon ring having from 3 to 12 ring members;

$R_{07}$ and $R_{08}$ each together with the C=C group to which they are bonded form a hydrocarbon ring or heterohydrocarbon ring having from 3 to 12 ring members;

$R_{07}$ and $R_{11}$, each together with the C=N group to which they are bonded form a hydrocarbon ring or heterohydrocarbon ring having from 3 to 12 ring members;

the hetero atoms in the heterocyclic rings being selected from the group O, S and N; and $R_{07}$, $R_{08}$, $R_{09}$, $R_{10}$ and $R_{11}$ are unsubstituted or substituted by $C_1$–$C_6$alkyl, $C_1$–$C_6$alkoxy, cyclohexyl, $C_6$–$C_{10}$aryl, $C_7$–$C_{12}$aralkyl, $C_1$–$C_4$alkyl-$C_6$–$C_{10}$aryl, $C_1$–$C_4$alkoxy-$C_6$–$C_{10}$aryl, $C_1$–$C_4$alkyl-$C_7$–$C_{12}$aralkyl, $C_1$–$C_4$alkoxy-$C_7$–$C_{12}$aralkyl, —OH, =O, —CO—OR$_{12}$, —CO—NR$_{13}$R$_{14}$ or by —NR$_{13}$R$_{14}$, wherein $R_{12}$ is H, an alkali metal, $C_1$–$C_6$alkyl, cyclohexyl, phenyl or benzyl, and $R_{13}$ and $R_{14}$ are each independently of the other hydrogen, $C_1$–$C_6$alkyl, cyclohexyl, phenyl or benzyl, or $R_{13}$ and $R_{14}$ together are tetramethylene, pentamethylene or 3-oxapentylene.

Examples and preferences for substituents have been given above.

$R_{07}$ and $R_{08}$ may be, for example, $C_1$–$C_{20}$alkyl and preferably $C_1$–$C_{12}$alkyl, $C_1$–$C_{20}$heteroalkyl and preferably $C_1$–$C_{12}$heteroalkyl having hetero atoms selected from the group O, S and N, $C_3$–$C_{12}$cycloalkyl and preferably $C_4$–$C_8$cycloalkyl, C-bonded $C_3$–$C_{11}$heterocycloalkyl and preferably $C_4$–$C_8$heterocycloalkyl having hetero atoms selected from the group O, S and N, $C_3$–$C_{12}$cycloalkyl-$C_1$–$C_6$alkyl and preferably $C_4$–$C_8$cycloalkyl-$C_1$–$C_6$alkyl, $C_3$–$C_{11}$heterocycloalkyl-$C_1$–$C_6$alkyl and preferably $C_4$–$C_8$heterocycloalkyl-$C_1$–$C_6$alkyl having hetero atoms selected from the group O, S and N, $C_6$–$C_{14}$aryl and preferably $C_6$–$C_{10}$aryl, $C_5$–$C_{13}$heteroaryl and preferably $C_5$–$C_9$heteroaryl having hetero atoms selected from the group O, S and N, $C_7$–$C_{15}$aralkyl and preferably $C_7$–$C_{11}$aralkyl, $C_6$–$C_{12}$heteroaralkyl and preferably $C_6$–$C_{10}$heteroaralkyl having hetero atoms selected from the group O, S and N.

When $R_{07}$ and $R_{08}$, $R_{07}$ and $R_{09}$, or $R_{07}$ and $R_{11}$, in each case together with the group to which they are bonded, form a hydrocarbon ring or heterohydrocarbon ring, that ring preferably contains from 4 to 8 ring members. The heterohydrocarbon ring may contain, for example, from 1 to 3, preferably one or two, hetero atoms.

$R_{11}$ is preferably hydrogen, $C_1$–$C_6$alkyl, $C_1$–$C_6$alkoxy, $C_4$–$C_8$cycloalkyl, $C_4$–$C_8$cycloalkyl-$C_1$–$C_4$alkyl, $C_4$–$C_{10}$heterocycloalkyl, $C_4$–$C_{10}$heterocycloalkyl-$C_1$–$C_4$alkyl, $C_6$–$C_{10}$aryl, $C_5$–$C_9$heteroaryl, $C_7$–$C_{12}$aralkyl or $C_5$–$C_{13}$heteroaralkyl.

Some examples of unsaturated organic compounds are acetophenone, 4-methoxyacetophenone, 4-trifluoromethylacetophenone, 4-nitroacetophenone, 2-chloroacetophenone, corresponding unsubstituted or N-substituted acetophenonebenzylimines, unsubstituted or substituted benzocyclohexanone or benzocyclopentanone and corresponding imines, imines from the group of unsubstituted or substituted tetrahydroquinoline, tetrahydropyridine and dihydropyrrole, and unsaturated carboxylic acids, esters, amides and salts, for example α- and optionally β-substituted acrylic acids or crotonic acids. Preferred carboxylic acids are those of the formula

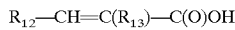

$$R_{12}\text{—CH}=C(R_{13})\text{—}C(O)OH$$

and their salts, esters and amides, wherein $R_{12}$ is $C_1$–$C_6$alkyl; $C_3$–$C_8$cycloalkyl unsubstituted or substituted by from 1 to 4 $C_1$–$C_6$alkyl, $C_1$–$C_6$alkoxy or $C_1$–$C_6$alkoxy-$C_1$–$C_4$alkoxy substituents, or $C_6$–$C_{10}$aryl, preferably phenyl, unsubstituted or substituted by from 1 to 4 $C_1$–$C_6$alkyl, $C_1$–$C_6$alkoxy or $C_1$–$C_6$alkoxy-$C_1$–$C_4$alkoxy substituents; and $R_{13}$ is linear or branched $C_1$–$C_4$$C_1$–$C_6$alkyl (for example isopropyl) or, unsubstituted or substituted as defined above, cyclopentyl, cyclohexyl, phenyl or protected amino (for example acetylamino).

The process according to the invention can be carried out at low or elevated temperatures, for example from −20 to 150° C., preferably from −10 to 100° C., more especially from 10 to 80° C. The optical yields are generally better at lower temperature than at higher temperatures.

The process according to the invention can be carried out at normal pressure or excess pressure. The pressure may be, for example, from $10^5$ to $2\times 10^7$ Pa (Pascal). Hydrogenations can be carried out at normal pressure or at excess pressure. Better selectivities are often observed at normal pressure.

Catalysts are used preferably in amounts of from 0.0001 to 10 mol %, especially from 0.001 to 10 mol %, more especially from 0.01 to 5 mol %, based on the compound to be hydrogenated.

The preparation of the ligands and catalysts and also the addition reaction can be carried out without a solvent or in the presence of an inert solvent, it being possible to use one solvent or a mixture of solvents. Examples of suitable solvents are aliphatic, cycloaliphatic and aromatic hydrocarbons (pentane, hexane, petroleum ether, cyclohexane, methylcyclohexane, benzene, toluene, xylene), aliphatic halogenated hydrocarbons (methylene chloride, chloroform, di- and tetra-chloroethane), nitrites (acetonitrile, propionitrile, benzonitrile), ethers (diethyl ether, dibutyl ether, tert-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic acid esters and lactones (ethyl or methyl acetate, valerolactone), N-substituted lactams (N-methylpyrrolidone), carboxylic acid amides (dimethylamide, dimethylformamide), acyclic ureas (dimethylimidazoline), and sulfoxides and sulfones (dimethyl sulfoxide, dimethyl sulfone, tetramethylene sulfoxide, tetramethylene sulfone) and alcohols (methanol, ethanol, propanol, butanol, ethylene glycol monomethyl ether, ethylene glycol monoethyl ether, diethylene glycol monomethyl ether) and water. The solvents can be used on their own or in a mixture of at least two solvents.

The reaction can be carried out in the presence of co-catalysts, for example quaternary ammonium halides (tetrabutylammonium iodide) and/or in the presence of protonic acids, for example mineral acids (see, for example, U.S. Pat. Nos. 5,371,256, 5,446,844 and 5,583,241 and EP-A-0 691 949). The co-catalysts are especially suitable for hydrogenations.

The metal complexes used as catalysts can be added in the form of separately prepared isolated compounds or alternatively they can be formed in situ prior to the reaction and then mixed with the substrate to be hydrogenated. It may be advantageous, when isolated metal complexes are being used in the reaction, additionally to add ligands or, in the case of in situ preparation, to use the ligands in excess. The excess may be, for example, from 1 to 10 mol, preferably from 1 to 5 mol, based on the metal compound used for preparation.

The process according to the invention is generally carried out by first introducing the catalyst into the reaction vessel and then adding the substrate, optionally reaction auxiliaries and the addition reaction compound and subsequently starting the reaction. Compounds to be added that are in gaseous form, for example hydrogen or ammonia, are preferably introduced under pressure. The process can be carried out continously or intermittently in various types of reactor.

The chiral organic compounds that can be prepared according to the invention are active ingredients or intermediates in the preparation of such ingredients, especially in the field of the manufacture of pharmaceuticals and agrochemicals. For example, o,o-dialkyl aryl-ketamine derivatives, especially those having alkyl and/or alkoxyalkyl groups, are effective as fungicides, especially as herbicides. The derivatives may be amine salts, acid amides, for example of choroacetic acid, tertiary amines and ammonium salts (see e.g. EP-A-0 077 755 and EP-A-0 115 470).

The following Examples illustrate the invention. Chromatographic separation and purification is carried out using C-Gel C-560 (Uetikon AG, Switzerland).

A) PREPARATION OF INTERMEDIATES

Example A1

Preparation of

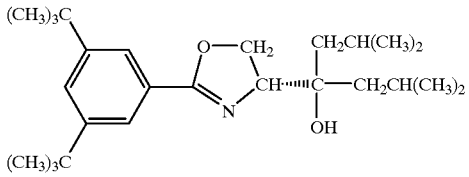

(A1)

a) Preparation of (−)—N-(1-carboxymethyl-2-hydroxy-ethyl)-3,5-di-tert-butylbenzamide (A1a)

2.53 g (16.3 mmol) of D-serine methyl ester hydrochloride are suspended in 50 ml of dichloromethane, and at 0° C. 2.23 g (16.3 mmol) of diisopropylethylamine and 3.81 g (16.3mmol) of 3,5-di-tert-butylbenzoic acid are added in succession thereto. After the addition of 3.7 g (19.6 mmol) of N-(3-dimethylaminopropyl)-N'-ethyl-carbodiimide hydrochloride (EDC), a homogeneous yellow solution is formed which is stirred at room temperature (RT) for 3 h. Extraction is then carried out with water and NH$_4$Cl solution (each 3×25 ml), the organic phase is dried over MgSO$_4$ and after column chromatography (15×4 cm, hexane/ethyl acetate 3:2) 5.4 g (99% of theory) of a colourless solid are obtained.

$^1$H-NMR (400 MHz, CDCl$_3$): 1.35 (s, 18H, CH$_3$—C); 3.84 (s, 3H, CH$_3$—O); 4.08 (dd, J=6.06/3.79, 2H, CH$_2$—O); 4.88 (dt, J=6.82/3.79, 1H, CH—N); 7.05 (d, J=6.82, 1H, NH); 7.60 (t, J=1.76, 1H, Ar—H); 7.63 (d, J=1.76, 1H, Ar—H).

$^{13}$C-NMR (100 MHz, CDCl$_3$): 31.7 (6C, CH$_3$); 35.3 (2C, Cq—C); 53.2 (1C, CH$_3$—O); 55.7 (1C, CH$_2$—N); 64.2 (1C, CH$_2$—O); 121.6 (2C, Ar—H); 126.6 (1C, Ar—H); 133.5 (1C, Ar—C=O); 151.8 (2C, Ar—CCH$_3$). α$_D$ (25° C., CHCl$_3$, c=1.0)=−30.5.

b) Preparation of (−)—N-(2-hydroxy-1-hydroxymethyl-3-isobutyl)-3,5-di-tert-butylbenzamide (A1b)

1.62 g (4.8 mmol) of compound A1a are dissolved in 20 ml of diethyl ether and cooled to −78° C., and 10 ml (20 mmol) of 2M isobutylmagnesium chloride solution in diethyl ether are slowly added thereto. Stirring is carried out at RT for 12 h, NH$_4$Cl solution is added at 0° C., the aqueous phase is extracted with diethyl ether (3×10 ml) and the combined organic phases are dried over MgSO$_4$. Column chromatography (15×3 cm, hexane/ethyl acetate 2:1) yields 664 mg (33%) of white solid.

$^1$H-NMR (300 MHz, CDCl$_3$): 0.93 (d, J=6.6, 3H, CH$_3$); 0.99 (d, J=6.5, 3H, CH$_3$); 1.01 (d, J=6.6, 3H, CH$_3$); 1.06 (d, J=6.4, 3H, CH$_3$); 1.35 (s, 18H, CH$_3$); 1.59 (d, J=5.8, 2H, CH$_2$); 1.60 (s, 1H, OH); 1.65 (d, J=6.0, 2H, CH$_2$); 1.75 (quint, J=6.5, 1H, CH); 1.87 (quint, J=6.3, 1H, CH); 2.73 (sbr, 1H, OH); 3.98–4.16 (m, 3H, Ox—H): 7.07 (d, J=7.6, 1H, NH); 7.59 (t, J=1.8, 1H, Ar—H); 7.64 (d, J=1.8, 2H, Ar—H).

$^{13}$C-NMR (75 MHz, CDCl$_3$): 23.9 (1C, CH$_3$); 24.1 (1C, CH$_3$); 24.3 (1C, CH$_3$); 24.4 (1H, CH$_3$); 24.8 (1C, CH); 25.1 (1C, CH); 31.3 (6C, CH$_3$); 34.9 (2C, Cq); 44.6 (1C, CH$_2$); 45.6 (1C, CH$_2$); 55.7 (1C, CH—N); 63.4 (1C, CH$_2$—O); 78.3 (1C, Cq—O); 121.1 (2C, Ar—H); 125.8 (1C, Ar—H); 134.1 (1C, Ar—C=C); 151.1 (2C, Ar—C—C); 168.7 (1C, C=N); 211.2 (1C, C=O).

c) Preparation of Title Compound A1

664 mg (1.58 mmol) of compound A1b 16 are dissolved in 10 ml of dichloromethane, and heated at reflux for 4 h with 2 ml of triethylamine and 386 mg (2.0 mmol) of p-toluenesulfonyl chloride. After the addition of 2 ml of water, the reaction mixture is again heated at reflux for 2 h, extracted with NH$_4$Cl solution (3×5 ml) and dried over MgSO$_4$. Column chromatography (15×2 cm, hexane/ethyl acetate 7:1) yields 358 mg (56% of theory) of a colourless amorphous solid.

Example A2

Preparation of

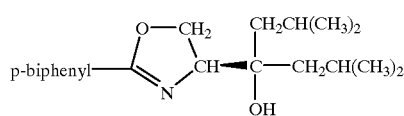

(A2)

a) Preparation of (+)-N-(1-carboxymethyl-2-hydroxy)ethylbiphenylcarbamide (A2a)

Preparation is carried out analogously to Example A1a using L-serine methyl ester hydrochloride and 1,1'-biphenyl-4-carboxylic acid. 1.6 g (36% of theory) of a colourless solid are obtained.

$^1$H-NMR (300 MHz, CDCl$_3$): 0.91 (d, J=6.5, 3H, CH$_3$); 0.98 (d, J=6.5, 3H, CH$_3$); 1.00 (d, J=7.5, 3H, CH$_3$); 1.06 (d, J=6.5, 3H, CH$_3$); 1.58 (d, J=6.5, 2H, CH$_2$); 1.66 (d, J=6.0, 2H, CH$_2$); 1.68–1.77 (m, 1H, CH); 1.80–1.91 (m, 1H, CH); 4.07–4.17 (m, 3H, CH$_2$O, CHN); 7.14 (d, J=9; 1H, NH); 7.38–7.49 (m, 3H, ArH); 7.59–7.68 (m, 4H, ArH); 7.88–7.91 (m, 2H, ArH).

$^{13}$C-NMR (75 MHz, CDCl$_3$): 24.0, 24.3, 24.8, 25.1 (6C, CH$_3$, CH); 31.3 (2C, CH$_2$); 55.3 (CH$_2$O); 76.8 (CHN); 79.3 (qC); 127.2–128.9 (aromatic C); 211 (C=O). α$_D$(25° C., c=0.64, CHCl$_3$)=+46.8.

b) Preparation of (+)-N-(2-hydroxy-1-hydroxymethyl-2-isobutyl-3-methyl)pentyl-biphenyl-carbamide Preparation is carried out analogously to Example A1b. Column chromatography (15×3 cm, hexane/ethyl acetate 3:1) gives a yield of 43%.

$^1$H-NMR (300 MHz, CDCl$_3$): 0.91 (d, J=6.5, 3H, CH$_3$); 0.98 (d, J=6.5, 3H, CH$_3$); 1.00 (d, J=7.5, 3H, CH$_3$); 1.06 (d, J=6.5, 3H, CH$_3$); 1.58 (d, J=6.5, 2H, CH$_2$); 1.66 (d, J=6.0, 2H, CH$_2$); 1.68–1.77 (m, 1H, CH); 1.80–1.91 (m, 1H, CH); 4.07–4.17 (m, 3H, CH$_2$O, CHN); 7.14 (d, J=9; 1H, NH); 7.38–7.49 (m, 3H, ArH); 7.59–7.68 (m, 4H, ArH); 7.88–7.91 (m, 2H, ArH).

$^{13}$C-NMR (75 MHz, CDCl$_3$): 24.0, 24.3, 24.8, 25.1 (6C, CH$_3$, CH); 31.3 (2C, CH$_2$); 55.3 (CH$_2$O); 76.8 (CHN); 79.3 (qC); 127.2–128.9 (aromatic C); 211 (C=O).

c) Preparation of the Title Compound

Preparation is carried out analogously to Example A1c. 89 mg (43% of theory) of a colourless oil are obtained.

$^1$H-NMR (300 MHz, CDCl$_3$): 0.87 (d, J=6.6, 3H, CH$_3$); 0.93 (d, J=6.5, 3H, CH$_3$); 0.95 (d, J=6.5, 3H, CH$_3$); 0.96 (d,

J=6.6, 3H, CH$_3$); 1.21 (dd, J=14.7/ 5.5, 1H, CH$_2$); 1.38 (dd, J=14.5/6.6, 1H, CH$_2$); 1.47 (s, 1H, OH); 1.56 (dd, J=14.7/ 7.1, 1H, CH$_2$); 1.66 (dd, J=14.5/5.1, 1H, CH$_2$); 1.71–1.86 (m, 2H, CH); 4.28–4.37 (m, 3H, Ox—H); 7.31 –7.42 (m, 3H, Ar—H); 7.53–7.59 (m, 4H, Ar—H); 7.94–7.97 (m, 2H, Ar—H).

$^{13}$C-NMR (100 MHz, CDCl$_3$): 24.2, 24.4, 24.9 (3C, CH$_3$); 25.2, 25.3 (CH); 44.2, 46.1 (CH$_2$); 69.0 (CH$_2$O); 74.6 (CHN); 76.5 (qC); 127–129 (aromatic C).

Example A3

Preparation of

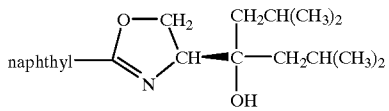

(A3)

a) Preparation of 1-{N-(1-carboxymethyl-2-hydroxy)}naphthylcarbamide 3 g (19.6 mmol) of L-serine methyl ester hydrochloride are dissolved in 100 ml of water and cooled to 0° C., and 3.1 g of NaHCO$_3$ are added thereto. After the addition of 3.7 g (19.5 mmol) of 1-naphthylcarbonyl chloride, stirring is carried out at RT for 72 hours. The aqueous suspension is extracted with chloroform and the organic extracts are dried over MgSO$_4$. After column chromatography (15×3 cm, hexane/ethyl acetate 1:1), 565 mg (11% of theory) of a colourless oil are obtained.

$^1$H-NMR (300 MHz, CDCl$_3$): 2.80 (sbr, 1H, OH); 3.95 (dd, J=11.1/3.4, 1H, CH$_2$O); 4.02 (dd, J=11.1/3.7, 1H, CH$_2$O); 4.85 (dt, J=7.7/3.7, 1H, CHN); 6.92 (d, J=7.35, 1H, NH); 7.34 (dd, J=7.1/8.25, 1H, ArH); 7.43–7.48 (m, 2H, ArH); 7.59 (dd, J=7.0/1.2, 1H, ArH); 7.76–7.85 (m, 2H, ArH); 8.26 (d, J=8.1, 1H, ArH).

$^{13}$C-NMR (75 MHz, CDCl$_3$): 52.8 (1C, OCH$_3$); 55.0 (1C, OCH$_2$); 63.2 (1C, NCH); 124.6 C3): 125.2 (C5); 126.4 (C9); 127.2 (C8); 128.3 (C10); 130.0 (C6); 131.0 (C7); 133.2 (C2); 133.6 (C$_1$); 169.8 (NC=O); 170.8 (OC=O).

b) Preparation of 1-(N-(2-hydroxy-1-hydroxymethyl-2-isobutyl-methyl)pentyl)-naphthyl-carbamide Preparation is carried out analogously to Example A1b. Column chromatography (15×2 cm, hexane/ethyl acetate 2:1) yields 661 mg (91%).

$^1$H-NMR (300 MHz, CDCl$_3$): 0.88 (d, J=6.5, 6H, CH$_3$); 0.90 (d, J=6.5, 3H, CH$_3$); 0.94 (d, J=6.5, 3H, CH$_3$); 1.48–1.53 (m, 4H, CH$_2$); 1.58–1.80 (m, 2H, CH); 2.81 (s, 1H, OH); 3.01 (s, 1H, OH); 3.90–4.07 (m, 3H, Ox—H); 6.89 (d, J=8.4, 1H, NH); 7.29 (dd, J=7.0/8.2, 1H, ArH); 7.41–7.45 (m, 2H, ArH); 7.51 (dd, J=7.0/1.2, 1H, ArH); 7.75–7.81 (m, 2H, ArH); 8.22–8.25 (m, 1H, ArH).

$^{13}$C-NMR (75 MHz, CDCl$_3$): 23.9 (1C, CH$_3$); 24.0 (1C, CH); 24.3 (2C, CH$_3$); 24.8 (1C, CH$_3$); 25.0 (1C, CH); 44.4 (1C, CH$_2$); 45.2 (1C, CH$_2$); 55.3 (1C, CHN); 63.3 (1C, OCH$_2$); 78.3 (1C, qC); 124.6,124.9, 125.3, 126.4, 127.1, 128.2 (1C, ArH); 130.1 (1C, ArC); 130.6 (1C, ArH); 133.6, 134.2 (1C, ArC); 169.7 (C=O).

c) Preparation of the Title Compound

Preparation is carried out analogously to Example A1c. Column chromatography (15×2 cm, hexane/ethyl acetate 4:1) yields 134 mg (62%).

$^1$H-NMR (300 MHz, CDCl$_3$): 0.90 (d, J=6.6, 3H, CH$_3$); 0.96 (d, J=6.6, 3H, CH$_3$); 0.97 (d, J=6.5, 3H, CH$_3$); 1.00 (d, J=6.6, 3H, CH$_3$); 1.29 (dd, J=14.5/5.4, 1H, CH$_2$); 1.42 (dd, J=14.5/6.8, 1H, CH$_2$); 1.47 (s,1H, OH); 1.62 (dd, J=14.5/6.8, 1H, CH$_2$); 1.72 (dd, J=14.5/5.2, 1H, CH$_2$); 1.83 (hept, J=6.5, 2H, CH); 4.30–4.40 (m, 2H, OCH$_2$); 4.51 (overlapping, dd, J=9.5, 1H, CHN); 7.40–7.56 (m, 3H, ArH); 7.81 (dd, J=7.9/ 6.2, 1H, ArH); 7.89 (d, J=8.2, 1H, ArH); 8.02 (dd, J=7.2/6.0, 1H, ArH); 9.07 (d, J=8.5, 1H, ArH).

$^{13}$C-NMR (100 MHz, CDCl$_3$): 24.2, 25.5 (CH$_3$); 24.9 (CH); 25.0 (CH$_3$); 25.3 (CH); 25.4 (CH$_3$); 44.4 (CH$_2$); 46.2 (CH$_2$); 67.9 (CH$_2$O); 75.3 (CHN); 76.6 (qC); 124.8, 125.0, 126.4, 126.8, 127.7, 128.9, 129.5 (NaphH); 131.6, 132.4, 134.1 (NaphC); 165.1 (C=N).

Example A4

Preparation of

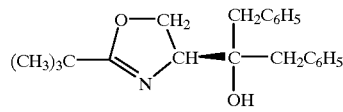

(A4)

a) Preparation of 2-tert-butyl4-carboxymethyl-oxazoline (A4a)

3 g (29.6 mmol) of pivalic acid amide are stirred with 5.6 g (29.6 mmol) of triethyloxonium tetrafluoroborate in 50 ml of dichloromethane for 48 h. Ammonia is passed through the solution over a period of 3 h, the resulting residue is filtered off and the filtrate is concentrated in a rotary evaporator. 4.67 g (30 mmol) of L-serine methyl ester hydrochloride are added with 50 ml of dichloroethane, and the mixture is then heated at reflux for 8 h. Extraction with NaHCO$_3$ solution and NH$_4$Cl solution, drying over MgSO$_4$ and purification by column chromatography (15×3 cm, pentane/diethyl ether 4:1) are carried out. Yield 1.34 g (24% of theory).

$^1$H-NMR (300 MHz, CDCl$_3$): 1.24 (s, 9H, CH$_3$); 3.78 (s, 3H, OCH$_3$); 4.37 (dd, J=8.7/10.5, 1H, CH$_2$O); 4.46 (dd, J=8.7/7.6, 1H, CH$_2$O); 4.71 (dd, J=10.5/7.6, 1H, CHN).

$^{13}$C-NMR (75 MHz, CDCl$_3$): 27.7 (3C, CH$_3$); 33.3 (1C, qC); 52.5 (1C, OCH$_3$); 68.1 (1C, OCH$_2$); 69.4 (1C, CHN); 176.9 (1C, C=O).

b) Preparation of A4

676 mg (3.6 mmol) of oxazoline A4a are dissolved in 10 ml of diethyl ether and cooled to −78° C., and 9 ml of 1M benzylmagnesium chloride solution in diethyl ether are added thereto. The mixture is stirred at room temperature (RT) for 60 h, extracted with NH$_4$Cl solution and dried over MgSO$_4$. Column chromatography (15×3 cm, pentane/ diethyl ether 4:1) yields 1.2 g of A1 (98% of theory).

$^1$H-NMR (300 MHz, CDCl$_3$): 1.16 (s, 9H, CH$_3$); 2.52 (d, J=13.7, 1H, CH$_2$Ar); 2.68 (s, 2H, CH$_2$Ar); 2.80 (d, J=13.7, 1H, CH$_2$Ar); 3.94–3.97 (m, 2H, CH$_2$O); 4.09 (dd, J=4.3/5.2, 1H, CHN); 7.15–7.29 (m, 1OH, ArH).

$^{13}$C-NMR (75 MHz, CDCl$_3$): 27.9 (3C, CH$_3$); 41.6 (1C, CH$_2$Ar); 41.9 (1C, CH$_2$Ar); 68.3 (1C, CH$_2$O); 71.6 (1C, CHN); 75.6 (1C, qC); 126.4 (4C, ArH); 128.1 (4C, ArH); 130.8 (1C, ArH); 130.9 (1C, ArH); 136.9 (1C, ArC); 137.0 (Arc).

Example A5

Preparation of

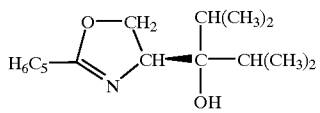

a) Preparation of 2-phenyl4-carboxymethyloxazoline (A5a)

567 mg (3.6 mmol) of L-serine methyl ester hydrochloride are dissolved in 0.5 ml of water, and 610 mg (3.6 mmol) of ethyl benzimidate in 10 ml of dichloromethane are added thereto. After 48 h at reflux, the mixture is concentrated to a volume of 50 ml of dichloromethane and washed with NaHCO$_3$ (3×10 ml), and the aqueous phase is extracted with ethyl acetate (2×10 ml). Column chromatography (15×5 cm, hexane/ethyl acetate 1:1) yields 3.0 g of A2a (91% of theory).

$^1$H-NMR (300 MHz, CDCl$_3$): 3.78 (s, 3H, OCH$_3$); 4.52–4.69 (m, 2H, CH$_2$O); 4.89–4.93 (m, 1H, CHN); 7.35–7.49 (m, 3H, ArH); 7.94–7.97 (m, 2H, ArH).

$^{13}$C-NMR (75 MHz, CDCl$_3$): 53.0 (OCH$_3$); 68.5 (CH$_2$O); 69.7 (CHN); 128.7, 128.9, 132.2 (ArH); 166.6 (C=N); 171.9 (C=O).

b) Preparation of A5

Preparation is carried out analogously to Example A4b using isopropylmagnesium chloride and compound A5a. Column chromatography (15×3 cm, hexane/ethyl acetate 6:1) yields 300 mg (20% of theory).

$^1$H-NMR (400 MHz, CDCl$_3$): 0.94 (d, J=6.8, 3H, CH$_3$); 0.97 (d, J=6.8, 3H, CH$_3$); 0.99 (d, J=7.1, 3H, CH$_3$); 1.11 (d, J=7.1, 3H, CH$_3$); 1.95–2.04 (m, 1H, CH); 2.20–2.20 (m, 2H, CH, OH); 4.41 (dd, J=10.2/8.4, 2H, CH$_2$O); 4.62 (t, J=10.2, 1H, CHN); 7.25–7.50 (m, 3H, ArH); 7.93–7.98 (m, 2H, ArH).

$^{13}$C-NMR (100 MHz, CDCl$_3$): 18.3, 18.5, 18.7,18.7 (CH$_3$); 32.8, 33.9 (CH); 69.4 (CH$_2$O); 70.7 (CHN); 77.7 (qC); 128.1 (ArC); 128.6, 131.7 (ArH); 164.1 (C=N).

Example A6

Preparation of

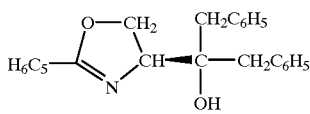

Title compound A6 is prepared analogously to Example A4b using compound A5a and benzylmagnesium chloride.

Example A7

Preparation of

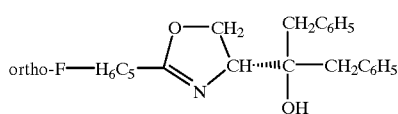

a) Preparation of 2-(1-fluorophenyl)-4-carboxymethyloxazoline (A5a)

878 mg (6.31 mmol) of 2-fluorobenzamide are stirred at RT with 1.2 g (6.31 mmol) of triethyloxonium tetrafluoroborate in 50 ml of dichloroethane. The precipitated solid is filtered off, washed with diethyl ether, dissolved in 50 ml of NaHCO$_3$ solution, and the aqueous solution is extracted with dichloroethane (5×20 ml). After the addition of 980 mg of D-serine methyl ester hydrochloride, the mixture is heated at reflux for 60 hours, filtered when cold and washed with NaCl solution. Column chromatography (15×3 cm, hexane/ethyl acetate 1:1) yields 1.08 g (71% of theory) of A7a.

$^1$H-NMR (200 MHz, CDCl$_3$): 3.81 (s, 3H, OCH$_3$); 4.50–4.72 (m, 2H, CH$_2$O); 4.99 (dd, J=7.9/2.8, 1H, NCH); 7.10–7.22 (m, 2H, ArH); 7.43–7.53 (m, 1H, ArH); 7.93 (dt, J=8/1.9, 1H, ArH).

$^{13}$C-NMR (50 MHz, CDCl$_3$): 52.3 (OCH$_3$); 68.2 (OCH$_2$); 69.0 (CHN); 116.3 (d, J$_{CF}$=21.8 ArH); 123.6 (d, J$_{CF}$=3.6, ArH); 131.0 (ArH); 133.1 (d, J$_{CF}$=8.7, ArH); 160.9 (d, J$_{CF}$=259, ArF); 171.0 (ArC).

b) Preparation of compound A7

Preparation is carried out analogously to Example A4b using compound A7a and benzyl-magnesium chloride. Column chromatography (15×2 cm, hexane/tert-butyl methyl ether 4:1) yields 264 mg of A7 (29% of theory).

$^1$H-NMR (200 MHz, CDCl$_3$): 2.01 (sbr, 1H, OH); 2.69 (d, J=13.7, 1H, CH$_2$Ar); 2.88 (s, 2H, CH$_2$Ar); 3.00 (d, J=13.7, 1H, CH$_2$Ar); 4.18–4.39 (m, 3H, CH$_2$0, CHN); 7.22–7.31 (m, 12H, ArH); 7.40–7.51 (m, 1H, ArH); 7.86–7.94 (m, 1H, ArH).

$^{13}$C-NMR (50 MHz, CDCl$_3$): 41.8, 41.9 (CH$_2$Ar); 68.1 (CH$_2$O); 71.6 (CHN); 75.4 (qC); 116.3 (d, J$_{CF}$=21.8, ArH); 123.5–130.9 (14 ArH); 132.5 (d, J$_{CF}$=17.6, ArH); 136.3, 136.4 (ArCH$_2$).

Example A8

Preparation of

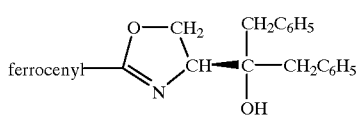

a) Preparation of N-(1-carboxymethyl-2-hydroxy) ethyl-ferrocenecarbamide 431 mg (2.2 mmol) of N-(3-dimethylaminopropyl)-N'-ethylcarbodiimide hydrochloride (EDC) and 350 mg (2.2 mmol) of L-serine methyl ester hydrochloride are added at 0° C. to 510 mg (2.2 mmol) of ferrocenecarboxylic acid in 5 ml dichloromethane, 363 mg (2.6 mmol) of 1-hydroxybenzotriazole (HOBT) in 2 ml of dimethylformamide (DMF) and 73 mg (0.55 mmol) of $CuCl_2$. After the addition of 300 mg (3.0 mmol) of triethylamine, the mixture is stirred at RT for 16 h and then extracted with $NH_4Cl$ solution, NaCl solution and $NHCO_3$ solution (each 2×10 ml). The aqueous phases are extracted again with ethyl acetate and dried over $MgSO_4$. After recrystallisation from ethyl acetate, 618 mg (80%) of reddish-brown solid are obtained.

b) Preparation of N-(2-hydroxy-1-methylhydroxy-1-methylphenyl-3-phenyl)propyl-ferrocenecarbamide Preparation is carried out analogously to Example A4b using benzylmagnesium chloride. Column chromatography (15×3 cm, hexane/ethyl acetate 2:1) yields 194 mg (45%) of solid.

$^1$H-NMR (400 MHz, $CDCl_3$): 2.65 (s, 1H, OH); 2.68 (d, J=14.1, 1H, $CH_2$—Ar); 2.96 (d, J=14.1, 1H, $CH_2$—Ar); 3.01 (d, J=13.8, 1H, $CH_2$—Ar); 3.04 (d, J=14.1, 1H, $CH_2$—Ar); 3.08 (sbr, 1H, OH); 4.04 (mbr, 2H, $CH_2$—O); 4.10–4.13 (mbr, 1H, CH—N); 4.18 (s, 5H, Cp—H); 4.31 (mbr, 2H, Cp—H); 4.42 (mbr, 1H, Cp—H); 4.52 (mbr, 1H, Cp—H); 6.22 (d, J=7.58, 1H, NH); 7.24–7.27 (m, 4H, Ar—H); 7.30–7.37 (m, 6H, Ar—H).

$^3$C-NMR (80 MHz, $CDCl_3$): 42.8 (1C, $CH_2$—Ar); 43.8 (1C, $CH_2$—Ar); 57.2 (1C, $CH_2O$); 63.6 (1C, CH—N); 68.0 (1C, Cp—H); 68.0 (1C, Cp—H); 69.7 (5C, Cp—H); 70.5 (1C, Cp—H); 76.1 (1C, Cp—H); 76.4 (1C, Cp—H); 77.2 (1C, Cp—C); 77.6 (1C, C—O); 127.0 (1C, Ar—H); 127.0 (1C, Ar—H); 128.6 (2C, Ar—H); 130.7 (2C, Ar—H); 130.8 (2C, Ar—H); 134.4 (1C, Ar—C); 136.4 (1C, Ar—C); 170.0 (1C, C=N).

c) Preparation of the Title Compound

Preparation is carried out analogously to Example A4b using benzylmagnesium chloride. Column chromatography (15×3 cm, hexane/ethyl acetate 2:1) yields 80 mg (94%) of solid.

$^1$H-NMR (400 MHz, $CDCl_3$): 2.65 (s, 1H, OH); 2.68 (d, J=14.1, 1H, CH2—Ar); 2.96 (d, J=14.1, 1H, $CH_2$—Ar); 3.01 (d, J=13.8, 1H, $CH_2$—Ar); 3.04 (d, J=14.1, 1H, $CH_2$—Ar); 3.08 (sbr, 1H, OH); 4.04 (mbr, 2H, $CH_2$—O); 4.10–4.13 (mbr, 1H, CH—N); 4.18 (s, 5H, Cp—H); 4.31 (mbr, 2H, Cp—H); 4.42 (mbr, 1H, Cp—H); 4.52 (mbr, 1H, Cp—H); 6.22 (d, J=7.58, 1H, NH); 7.24–7.27 (m, 4H, Ar—H); 7.30–7.37 (m, 6H, Ar—H).

$^{13}$C-NMR (80 MHz, $CDCl_3$): 42.8 (1C, $CH_2$—Ar); 43.8 (1C, $CH_2$—Ar); 57.2 (1C, $CH_2$—O); 63.6 (1C, CH—N); 68.0 (1C, Cp—H); 68.0 (1C, Cp—H); 69.7 (5C, Cp—H); 70.5 (1C, Cp—H); 76.1 (1C, Cp—H); 76.4 (1C, Cp—H); 77.2 (1C, Cp—C); 77.6 (1C, C—O); 127.0 (1C, Ar—H); 127.0 (1C, Ar—H); 128.6 (2C, Ar—H); 130.7 (2C, Ar—H); 130.8 (2C, Ar—H); 134.4 (1C, Ar—C); 136.4 (1C, Ar—C); 170.0 (1C, C=N).

Example A9
Preparation of

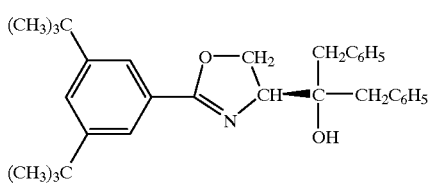

(A9)

a) Preparation of 4-carboxymethyl-2-(3,5-di-tert-butyl)phenyl-oxazoline (A9a)

415 mg (1.6 mmol) of 3,5-di-tert-butyl benzimidate are heated at reflux for 18 h with 250 mg (1.6 mmol) of L-serine methyl ester hydrochloride in 20 ml of dichloroethane. After extraction with $NaHCO_3$ solution and NaCl solution (each 2×5 ml), drying over $MgSO_4$ is carried out, followed by column chromatography (15×3 cm, diethyl ether/pentane 1:3), yielding 342 mg (68%) of a colourless oil.

$^1$H-NMR (400 MHz, $CDCl_3$): 1.34 (s, 9H, $CH_3$); 3.81 (s, 3H, $OCH_3$); 4.57 (dd, J=10.6/8.6, 1H, $OCH_2$); 4.68 (dd, J=7.8/8.6, 1H, $OCH_2$); 4.95 (dd, J=10.6/7.8, 1H, NCH); 7.56 (t, J=1.7, ArH); 7.81 (d, J=1.7, 2H, ArH).

$^{13}$C-NMR (125 MHz, $CDCl_3$): 31.7 (9C, $CH_3$); 35.3 (2C, qC); 53.0 (1C, $OCH_3$); 69.1 (1C, CHN); 69.8 (1C, $OCH_2$); 123.2 (1C, ArH); 126.5 (1C, ArH); 126.6 (1C, ArH); 151.4 (2C, ArC); 167.5 (1C, C=N); 172.2 (1C, C=O).

b) 4-(1-Benzyl-1-hydroxy-2-phenyl)ethyl-2-(3,5-di-tert-butylphenyl)oxazoline (A9b)

181 mg (0.57 mmol) of compound A9a are dissolved in 20 ml of diethyl ether and cooled to −78° C. After the addition of 14 ml of a 1M benzylmagnesium chloride solution, the mixture is heated to RT, extracted with $NH_4Cl$ solution and NaCl solution and dried over $MgSO_4$. Column chromatography (15×2 cm, pentane/diethyl ether 2:1) yields 231.3 g (86%) of a colourless, amorphous solid.

$^1$H-NMR (400 MHz, $CDCl_3$): 1.35 (s, 18H, $CH_3$); 2.01 (s, 1H, OH); 2.69 (d, J=13.9, 1H, $CH_2Ar$); 2.90 (s, 2H, $CH_2Ar$); 2.98 (d, J=13.6, 1H, $CH_2Ar$); 4.19–4.35 (m, 3H, $CH_2O$, CHN); 7.19–7.33 (m, 1 OH, BnH); 7.56 (t, J=1.7, 1H, ArH); 7.81 (d, J=1.7, 2H, ArH).

$^{13}$C-NMR (100 MHz, $CDCl_3$): 31.8 (6C, $CH_3$); 35.3 (2C, qC); 42.4, 42.9 ($CH_2Ar$); 68.7 ($CH_2O$); 72.8 (qC); 76.4 (CHN); 123.0 (2C, BnH); 126.1, 126.8, 126.9 (ArH); 127.3 (ArC); 128.5, 131.3 (4C, BnH); 137.2, 137.5 ($ArCH_2$); 151.3 (2C, Ar'Bu); 165.9 (C=N).

Example A10
Preparation of

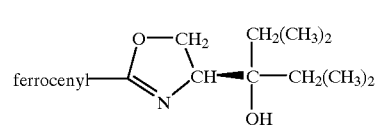

(A10)

a) Preparation of 4-carboxymethyl ester-2-ferrocenyl-oxazoline (A10a)

Preparation is carried out analogously to Example A9a. Column chromatography (15×3 cm, hexane/ethyl acetate 1:1) yields 1.4 g (78% of theory) of a reddish-brown solid.

$^1$H-NMR (300 MHz, $CDCl_3$): 3.82 (s, 3H, $OCH_3$); 4.22 (s, 5H, Cp—H); 4.37 (quartet, J=1.9, 2H, CpH); 4.46 (dd, J=10.2/8.7, 1H, $CH_2O$); 4.59 (dd, J=8.5/7.1, 1H, $CH_2O$); 4.78 (dd, J=10.1/7.1, 1H, CHN); 4.76–4.79 (m, 1H, CpH); 4.82–4.85 (m, 1H, CpH).

$^{13}$C-NMR (100 MHz, $CDCl_3$): 53.0 (1C, $OCH_3$); 68.9 (1C, $CH_2O$); 69.2 (1C, CpC); 69.7 (1C, CpH); 69.7 (1C, CpH); 70.1 (5C, CpH); 71.0 (1C, CpH); 71.1 (1C, CpH); 77.6 (1C, CHN); 169.9 (1C, C=N); 172.3 (1C, C=O).

b) Preparation of 2-ferrocenyl-4-(1-hydroxy-1-isopropyl-2-methyl)-oxazoline (A10b)

Preparation is carried out analogously to Example A9b using isopropylmagnesium chloride. Column chromatography (15×3 cm, hexane/ethyl acetate 1:1) yields 300 mg (53% of theory) of solid.

$^1$H-NMR (400 MHz, CDCl$_3$): 0.96 (d, J=6.8, 3H, CH$_3$); 0.97 (d, J=7.1, 3H, CH$_3$); 0.98 (d, J=7.1, 3H, CH$_3$); 1.11 (d, J=7.1, 3H, CH$_3$); 1.99 (septet, J=6.9, 1H, CH); 2.22 (septet, J=7.0, 1H, CH); 2.28 (s, 1H, OH); 4.19 (s, 5H, CpH); 4.27 (dd, J=8.1/9.8, 1H, CH$_2$O); 4.32 (m, 2H, CpH); 4.34 (dd, J=8.1/10.1, 1H, CH$_2$O); 4.45 (dd, J=9.8/10.1, 1H, CHN); 4.69–4.70 (m, 1H, CpH); 4.71–4.73 (m, 1H, CpH).

$^{13}$C-NMR (100 MHz, CDCl$_3$): 18.5 (2C, CH$_3$); 18.7 (1C, CH$_3$); 18.7 (1C, CH$_3$); 32.6 (1C, CH); 33.8 (1C, CH); 69.0 (1C, CpH); 69.3 (1C, CH$_2$O); 69.4 (1C, CpH); 69.8 (5C, CpH); 70.5 (1C, CHN); 70.6 (2C, CpH); 71.0 (1C, CpC); 77.6 (1C, qC); 166.4 (1C, C=N).

Example A11
Preparation of

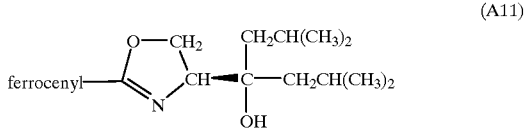
(A11)

Preparation is carried out analogously to Example A9b using isobutylmagnesium chloride. Column chromatography (15×3 cm, hexane/ethyl acetate 3:1) yields 500 mg (78% of theory) of solid.

$^1$H-NMR (400 MHz, CDCl$_3$): 0.94 (d, J=6.57, 3H, CH$_3$); 1.00 (d, J=6.3, 3H, CH$_3$); 1.01 (d, J=6.57, 3H, CH$_3$); 1.02 (d, J=6.3, 3H, CH$_3$); 1.25 (dd, J=14.4/5.2, 1H, CH$_2$); 1.45 (dd, J=14.6/6.7, 1H, CH$_2$); 1.56 (dd, J=14.6/7.0, 1H, CH$_2$); 1.64 (s, 1H, OH); 1.68 (dd, J=14.6/5.2, 1H, CH$_2$); 1.84 (dsept, J=6.5, 2H, CH); 4.22–4.31 (m, 3H, CH$_2$—O, CH—N); 4.34 (quin, J=1.2, 2H, Cp—H); 4.71–4.72 (m, 1H, Cp—H); 4.76–4.77 (m, 1H, Cp—H).

$^{13}$C-NMR (125 MHz, CDCl$_3$): 23.7 (1C, CH$_3$); 24.0 (1C, CH$_3$); 24.6 (2C, CH$_3$); 24.8 (1C, CH); 24.9 (1C, CH); 43.6 (1C, CH$_2$); 45.4 (1C, CH$_2$); 68.2 (1C, CH$_2$—O); 69.0 (2C, Cp—H); 69.5 (5C, Cp—H); 70.1 (1C, Cp—C); 70.2 (1C, C—pH); 70.3 (1C, Cp—H); 73.9 (1C, CH—N); 75.8 (1C, Cq); 167.3 (1C, C=N).

Example A12
Preparation of

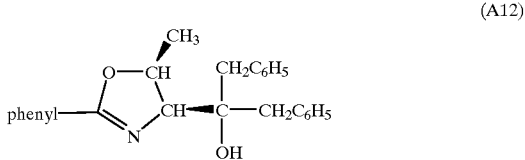
(A12)

a) Preparation of N-benzoyl-L-threonine methyl ester (A12a)

3.00 g (17.7 mmol/1 eq) of L-threonine methyl ester hydrochloride are suspended in 50 ml of methanol, and 7.4 ml (53 mmol/3 eq) of triethylamine are added thereto. After 10 minutes, the mixture is cooled to 0° C. and the benzoyl chloride (2.74 g/190.5 mmol/1.1 eq) is added. Stirring is carried out at 0° C. for a further two hours. The solvent is then removed using a rotary evaporator. The solid that remains behind is taken up with ethyl acetate/H$_2$O (50/20 ml). The aqueous phase is separated off and extracted by shaking twice more with ethyl acetate (30 ml each time). The combined organic phases are washed with 15 ml each of H$_2$O and saturated sodium chloride solution, dried over magnesium sulfate and concentrated. 4.07 g (97% of theory) of a white solid are obtained.

$^1$H-NMR (400 MHz, CDCl$_3$): δ=1.29 (d, $^3J_{HH}$=6.3 Hz, 3H, CH$_3$), 2.54 (s, 1H, OH), 3.80 (s, 3H, OCH$_3$), 4.45 (dq, $^3J_{HH}$=2.6 Hz, $^3J_{HH}$=6.3 Hz, 1H, CH—CH$_3$), 4.83 (dd, $^3J_{HH}$=2.6 Hz, $^3J_{HH}$=8.6 Hz, 1H, NH—CH), 6.93 (bd, $^3J_{HH}$=8.6 Hz, 1H, NH), 7.44 (t, $^3J_{HH}$=7.3 Hz, 2H, PhH), 7.47 (t, $^3J_{HH}$=7.3 Hz, 1H, PhH), 7.84 (d, $^3J_{HH}$=7.3 Hz, PhH).

b) Preparation of (4S,5S)-2-phenyl-4-carboxymethyl-5-methyl-oxazoline (A12b)

1.07 g (4.5 mmol/1 eq) of compound 12a are dissolved in 10 ml of tetrahydrofuran; 1.18 g (5.0 mmol/1.1 eq) of Burgess reagent are added and the mixture is heated at 70–80° C. for 2 h. The mixture is then allowed to cool and 5 ml of water are added. Extraction by shaking 3 times with 30 ml of dichloromethane is then carried out. After drying over magnesium sulfate and removal of the solvent, 0.890 g (95% of theory) of the oxazoline is obtained in the form of an oil which is used without further purification.

$^1$H-NMR (400 MHz, CDCl$_3$): δ=1.38 (d, $^3J_{HH}$=6.3 Hz, 3H, CH$_3$), 3.78 (s, 3H, OCH$_3$), 4.98 (d, $^3J_{HH}$=10.2 Hz, 1H, C=N—CH), 5.07 (dq, $^3J_{HH}$=6.3 Hz, $^3J_{HH}$=10.2 Hz, 1H, CH—CH$_3$), 7.42 (t, $^3J_{HH}$=7.3 Hz, 2H, PhH), 7.48 (t, $^3J_{HH}$=7.3 Hz, 1H, PhH), 7.98 (d, $^3J_{HH}$=7.3 Hz, 2H, PhH).

c) Preparation of A12

500 mg (2.28 mmol/1 eq) of compound A12b are dissolved in 10 ml of absolute diethyl ether and cooled to −78° C. 6.8 ml (6.8 mmol/3 eq) of a benzylmagnesium chloride solution (1M in hexane) are then slowly added dropwise thereto. During 12 hours' subsequent stirring, the reaction mixture assumes room temperature, a white solid being precipitated. The supernatant solution is yellow. It is poured into a cold ammonium chloride solution. After separation of the phases, extraction is carried out twice more with diethyl ether. The combined organic phases are washed with sodium hydrogen carbonate solution and sodium chloride solution and dried over magnesium sulfate. The solvent is removed in vacuo. After column chromatography (pentane/ether: 7/1), 690 mg (1.86 mmol/82%) of compound A12 are obtained in the form of a white microcrystalline solid.

$^1$H-NMR (400 MHz, CDCl$_3$): δ=1.73 (d, $^3J_{HH}$=6.8 Hz, 3H, CH$_3$), 2.00 (s, 1H OH), 2.69 (d, $^2J_{HH}$=13.6 Hz, 1H, Ph—CH$_2$), 2.93 (d, $^2J_{HH}$=13.9 Hz, 1H, Ph—CH$_2$), 3.11 (d, $^2J_{HH}$=13.9 Hz, 1H, Ph—CH$_2$), 3.19 (d, $^2J_{HH}$=13.6 Hz, 1H, Ph—CH$_2$), 4.11 (d, $^3J_{HH}$=9.6 Hz, 1H, C=N—CH), 4.84 (dq, $^3J_{HH}$=6.8 Hz, $^3J_{HH}$=9.6 Hz, 1H, CH—CH$_3$), 7.15–7.37 (m, 10H, BnH), 7.44 (t, $^3J_{HH}$=7.3 Hz, 2H, PhH), 7.50 (t, $^3J_{HH}$=7.3 Hz, 1H, PhH), 8.05 (d, $^3J_{HH}$=7.3 Hz, 2H, PhH).

Example A13

Preparation of

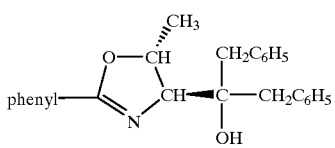

(A13)

a) Preparation of N-benzoyl-L-allo-threonine methyl ester (A13a)

Preparation is carried out analogously to Example A12a using L-allo-threonine methyl ester. 1.2 g (96% of theory) of a crystalline solid are obtained.

$^1$H-NMR (400 MHz, CDCl$_3$): δ=1.23 (d, $^3J_{HH}$=6.3 Hz, 3H, CH$_3$), 3.53 (s, 1H, OH), 3.83 (s, 3H, OCH$_3$), 4.29 (m, 1H, C$\underline{H}$—CH$_3$), 4.88 (dd, $^3J_{HH}$=3.3 Hz, $^3J_{HH}$=7.1 Hz, 1H, NH—C$\underline{H}$), 7.13 (bd, 1H, N$\underline{H}$), 7.44 (t, $^3J_{HH}$=7.3 Hz, 2H, PhH), 7.47 (t, $^3J_{HH}$=7.3 Hz, 1H, PhH), 7.84 (d, $^3J_{HH}$=7.3 Hz, PhH).

b) Preparation of (4S,5R)-2-phenyl-4-carboxymethyl-5-methyl-oxazoline (A13b)

Preparation is carried out analogously to Example A12b. 775 mg (80% of theory) of a colourless oil are obtained.

$^1$H-NMR (400 MHz, CDCl$_3$): δ=1.54 (d, $^3J_{HH}$=6.3 Hz, 3H, CH$_3$), 3.81 (s, 3H, OCH$_3$), 4.46 (d, $^3J_{HH}$=7.6 Hz, 1H, C=N—C$\underline{H}$), 4.98 (m, 1H, C$\underline{H}$—CH$_3$), 7.39 (t, $^3J_{HH}$=7.3 Hz, 2H, PhH), 7.48 (t, $^3J_{HH}$=7.3 Hz, 1H, PhH), 7.98 (d, $^3J_{HH}$=7.3 Hz, 2H, PhH).

c) Preparation of A13

Preparation is carried out analogously to Example A12c. 650 mg (77% of theory) are obtained in the form of a colourless solid.

$^1$H-NMR (400 MHz, CDCl$_3$): δ=1.28 (d, $^3J_{HH}$=6.3 Hz, 3H, CH$_3$), 1.77 (s, 1H, OH), 2.65 (d, $^2J_{HH}$=13.9 Hz, 1H, Ph—C$\underline{H}_2$), 2.77 (d, $^2J_{HH}$=13.9 Hz, 1H, Ph—C$\underline{H}_2$), 2.86 (d, $^2J_{Hh}$=13.6 Hz, 1H, Ph—C$\underline{H}_2$), 3.07 (d, $^2J_{HH}$=13.9 Hz, 1H, Ph—C$\underline{H}_2$), 3.80 (d, $^3J_{HH}$32 5.8 Hz, 1H, C=N—C$\underline{H}$), 4.89 (m, 1H, CH—CH$_3$), 7.17–7.35 (m, 10H, BnH), 7.43 (t, $^3J_{HH}$=7.3 Hz, 2H, PhH), 7.50 (t, $^3J_{HH}$=7.3 Hz, 1H, PhH), 8.05 (d, $^3J_{HH}$=7.3 Hz, 2H, PhH).

Example A14

Preparation of

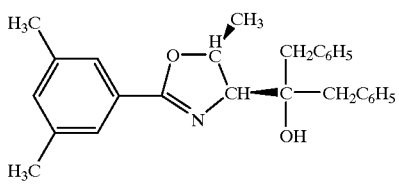

(A14)

a) Preparation of (3',5'-dimethylbenzoyl)-L-threonine methyl ester (A14a)

1.00 g (6.66 mmol/1 eq) of 3,5-dimethylbenzoic acid and 1.13 g (6.66 mmol/1 eq) of L-threonine methyl ester hydrochloride are suspended in 50 ml dichloromethane. At 0° C., 2.04 ml (14.7 mmol/2.2 eq) of triethylamine are added dropwise. After 10 minutes' stirring, 2.55 g (13.3 mmol/2 eq) of N-(3-dimethylaminopropyl)-N'-ethyl-carbodiimide hydrochloride (EDC) are added, and after a further 15 min 1-hydroxybenzotriazole (HOBt) is added. Stirring is carried out for twelve hours, the solution assuming room temperature. The organic phase is washed with 10 ml each of H$_2$O, hydrochloric acid (2N), and NaHCO$_3$ solution. After drying over magnesium sulfate, the solvent is removed in vacuo. 1.70 g (6.41 mmol/96%) of a white solid are obtained, which may, if desired, be recrystallised from absolute diethyl ether.

$^1$H-NMR (400 MHz, CDCl$_3$): δ1.28 (d, $^3J_{HH}$=6.3 Hz, 3H, CH$_3$), 2.35 (s, 6H, CH$_3$), 2.42 (s, 1H, OH), 3.79 (s, 3H, OCH$_3$), 4.45 (m, 1H, C$\underline{H}$—CH$_3$), 4.82 (dd, $^3J_{HH}$=2.5 Hz, $^3H_{HH}$=8.7 Hz, 1H, NH—C$\underline{H}$), 7.13 (bd, $^3J_{HH}$=8.7 Hz, 1H, NH), 7.14 (s, 1H, PhH), 7.44 (s, 2H, PhH).

b) Preparation of (4S,5S)-2-(3',5'-dimethylphenyl)-4-carboxymethyl-5-methyl-oxazoline (A14b)

Preparation is carried out analogously to Example A12b. 870 mg (78% of theory) of a colourless oil are obtained.

$^1$H-NMR (400 MHz, CDCl$_3$): δ=1.38 (d, $^3J_{HH}$=6.3 Hz, 3H, CH$_3$), 2.34 (s, 6H, CH$_3$), 3.78 (s, 3H, OCH$_3$), 4.96 (d, $^3J_{HH}$=10.4 Hz, 1H, C=N—C$\underline{H}$), 5.05 (m, 1H, C$\underline{H}$—CH$_3$), 7.12 (s, 1H, PhH), 7.61 (s, 2H, PhH).

c) Preparation of compound A14

Preparation is carried out analogously to Example A12b. 621 mg (69% of theory) of a colourless solid are obtained.

$^1$H-NMR (400 MHz, CDCl$_3$): δ=1.72 (d, $^3J_{HH}$=6.3 Hz, 3H, CH$_3$), 2.00 (s, 1H, OH), 2.38 (s, 6H, CH$_3$), 2.70 (d, $^2J_{HH}$=13.6 Hz, 1H, Ph—C$\underline{H}_2$), 2.92 (d, $^2J_{HH}$=13.9 Hz, 1H, Ph—C$\underline{H}_2$), 3.11 (d, $^2J_{HH}$=13.9 Hz, 1H, Ph—C$\underline{H}_2$), 3.19 (d, $^2J_{HH}$=13.6 Hz, 1H, Ph—C$\underline{H}_2$), 4.10 (d, $^3J_{HH}$=9.3 Hz, 1H, C=N—C$\underline{H}$), 4.82 (dq, $^3J_{HH}$=6.3 Hz, $^3J_{HH}$=9.3 Hz, 1H, C$\underline{H}$—CH$_3$), 7.14 (s, 1H, PhH), 7.19–7.35 (m, 10H, BnH), 7.64 (s, 2H, PhH).

Example A15

Preparation of

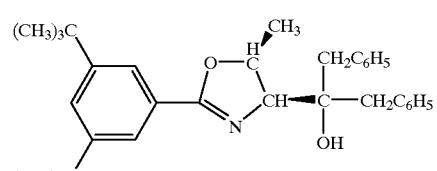

(A15)

a) Preparation of (3',5'-di-tert-butyl)benzoyl-L-threonine methyl ester (A15a)

Preparation is carried out analogously to Example A14a. 1.80 g (97% of theory) of a colourless solid are obtained.

$^1$H-NMR (400 MHz, CDCl$_3$): δ=1.30 (d, $^3J_{HH}$=6.3 Hz, 3H, CH$_3$), 1.34 (s, 18H, CCH$_3$), 2.39 (s, 1H, OH), 3.80 (s, 3H, OCH$_3$), 4.45 (m, 1H, C$\underline{H}$—CH$_3$), 4.83 (dd, $^3J_{HH}$=2.5 Hz, $^3J_{HH}$=8.6 Hz, 1H, NH—C$\underline{H}$), 6.90 (bd, $^3J_{HH}$=8.6 Hz, 1H, NH), 7.60 (s, 1H, PhH), 7.65 (s, 2H, PhH).

b) Preparation of (4S,5S)-2-(3',5'-di-tert-butyl) phenyl-4-carboxymethyl-5-methyl-oxazoline (A15b)

Preparation is carried out analogously to Example A12b. 1.17 g (71% of theory) of a colourless oil are obtained.

¹H-NMR (400 MHz, CDCl₃): δ=1.35 (s, 18H, CCH₃), 1.40 (d, ³J_HH=6.3 Hz, 3H, CH₃), 3.78 (s, 3H, OCH₃), 4.98 (d, ³J_HH=10.1 Hz, 1H, C=N—CH), 5.05 (m, 1H, CH—CH₃), 7.57 (s, 1H, PhH), 7.82 (s, 2H, PhH).

c) Preparation of compound A15

Preparation is carried out analogously to Example A12b. 1.07 mg (78% of theory) of a colourless solid are obtained.

¹H-NMR (400 MHz, CDCl₃): δ=1.38 (s, 18H, CCH₃), 1.73 (d, ³J_HH=6.3 Hz, 3H, CH₃), 2.15 (s, 1H, OH), 2.73 (d, ²J_HH=13.9 Hz, 1H, Ph—CH₂), 2.97 (d, ²J_HH=13.9 Hz, 1H, Ph—CH₂), 3.10 (d, ²J_HH=14.2 Hz, 1H, Ph—CH₂), 3.20 (d, ²J_HH=13.6 Hz, 1H, Ph—CH₂), 4.11 (d, ³J_HH=9.6 Hz, 1H, C=N—CH), 4.82 (dq, ³J_HH=6.3 Hz, ³J_HH=9.6 Hz, 1H, CH—CH₃), 7.24–7.35 (m, 10H, BnH), 7.58 (s, 1H, PhH), 7.86 (s, 2H, PhH),

B) Preparation of ligands

Example B1
Preparation of

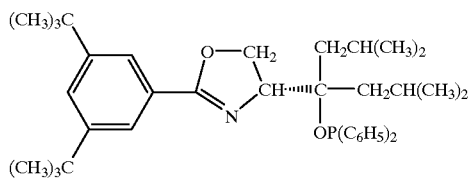
(B1)

Compound A1 is stirred at −78° C. with N,N,N',N'-tetramethylethylenediamine (TMEDA) (0.3 ml) in 5 ml of diethyl ether. 0.7 ml of 1.6M n-butyllithium solution is slowly added drop-wise thereto. Stirring is then carried out at RT for 1 h, and then 219 mg (0.99 mmol) of chlorodiphenylphosphine are added and stirring is carried out for 16 h. The solvent is removed and the solid is purified directly by column chromatography (15×2 cm, hexane/ethyl acetate, 15:1). 300 mg (57% of theory) of a colourless, amorphous solid are obtained.

¹H-NMR (300 MHz, CDCl₃): 0.89 (d, J=6.5, 6H, CH₃); 0.89 (d, J=6.5, 3H, CH₃); 0.93 (d, J=6.5, 3H, CH₃); 1.27 (s, 9H, CH₃); 1.75–1.91 (m, 6H, CH+CH₂); 4.07 (dd, J=10.3/8.3, 1H, Ox—H); 4.29 (t, J=8.3, 1H, Ox—H); 4.54 (dd, J=10.3/7.9, 1H, Ox—H); 7.05–7.07 (m, 2H, Ar—H); 7.17–7.20 (m, 3H, Ar—H); 7.32–7.37 (m, 2H, Ar—H); 7.42–7.47 (m, 3H, Ar—H); 7.6 (d, J=1.9, 2H, Ar—H).

³¹P-NMR (120 MHz, CDCl₃): 89.0 (s, OPAr₂).

Example B2
Preparation of

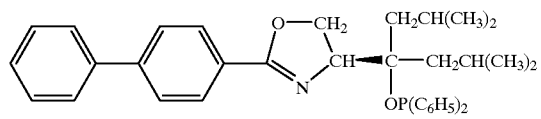
(B2)

Preparation is carried out analogously to Example B1 using compound A2. Column chromatography (15×2 cm, hexane/ethyl acetate 5:1) yields 70 mg (63%) of a solid.

¹H-NMR (300 MHz, CDCl₃): 0.84–0.97 (m, 12H, CH₃); 1.60–1.95 (m, 6H, CH₂, CH); 4.10 (t, 1H, CH₂O); 4.35 (t, 1H, CHN); 4.55 (t, 1H, CH₂O); 7.05–7.60 (m, 7H, ArH); 7.82 (d, 2H, ArH).

¹³C-NMR (75 MHz, CDCl₃): 23.5, 23.8 (CH); 25.0, 25.1, 25.2, 25.2 (CH₃); 43.6 (d, J_CP=9, CH₂); 45.5 (d, J_CP=6, CH₂); 68.8 (CH₂O); 73.6 (d, J_CP=3, CHN); 84.9 (d, J_CP=6, qC); 126.7–130.6 (aromatic C); 140.4 (ArP); 143.9 (d, J_CP=26, ArP); 163.7 (C=N).

³¹P—NMR (120 MHz, CDCl₃): 89.1 (OPAr₂).

Example B3
Preparation of

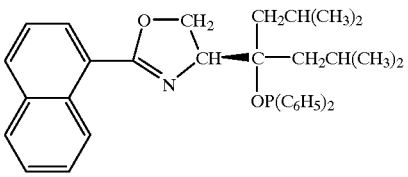
(B3)

Preparation is carried out analogously to Example B1 using compound A3. Column chromatography (15×2 cm, hexane/ethyl acetate 10:1) yields 105 mg (52%) of a solid.

¹H-NMR (300 MHz, CDCl₃): 0.88–0.95 (m, 9H, CH₃); 0.96 (d, J=6, 3H, CH₃); 1.65–2.01 (m, 6H, CH₂, CH); 4.12 (dd, J=10.1/8.8, 1H, CH₂O); 4.32 (t, J=8.4, 1H, CHN); 4.72 (dd, J=10.1/8.3, 1H, CH₂O); 7.00–7.17 (m, 4H, ArH); 7.29–7.46 (m, 6H, ArH); 7.79 (d, J=7.7, 2H, NaphH); 7.82 (d, J=7.9, 2H, NaphH); 7.87 (d, J=7.4, 2H, NaphH); 9.25 (d, J=8.2, 1H, NaphH).

³¹P-NMR (120 MHz, CDCl₃): 89.2 (OPAr₂).

Example B4
Preparation of

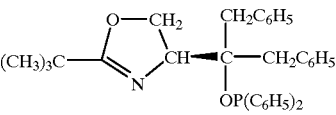
(B4)

Preparation is carried out analogously to Example B1 using compound A4. After column chromatography (15×2 cm, pentane/diethyl ether 10:1), 450 mg (26% of theory) of a yellowish solid are obtained.

¹H-NMR (400 MHz, CDCl₃): 1.22 (s, 9H, CH₃); 3.01–3.08 (m, 2H, CH₂Ar); 3.18 (dd, J=14.1/1.5, 1H, CH₂Ar); 3.41–3.48 (m, 2H, CH₂Ar, CH₂O); 3.70 (dd, J=8.8/7.8, 1H, CHN); 4.16–4.18 (m, 1H, CH₂O); 7.03–7.15 (m, 5H, ArH); 7.20–7.30 (m, 10H, ArH); 7.44–7.51 (m, 5H, ArH).

³¹P-NMR (160 MHz, CDCl₃): 84.2 (OPAr₂).

Example B5
Preparation of

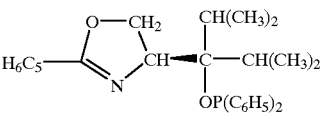
(B5)

Preparation is carried out analogously to Example B1 using compound A5. Column chromatography (15×2 cm, pentane/diethyl ether 10:1) yields 134 mg (34%) of a solid.

¹H-NMR (400 MHz, CDCl₃): 0.95 (d, J=7.1, 3H, CH₃); 1.07 (d, J=6.8, 3H, CH₃); 1.11, 1.19 (d, J=7.1, 3H, CH₃); 2.48 (dquintet, J=7.1/1.0, 1H, CH); 2.96 (dquintet, J=7.1/3.7, 1H, CH); 4.35 (dd, J=10.6/8.3, CH₂O); 4.44 (dd, J=9.3/8.3, CH₂O); 4.77 (t, J=9.9, CHN); 7.01–7.16 (m, 4H, ArH); 7.19–7.28 (m, 4H, ArH); 7.34–7.50 (m, 5H, ArH); 7.80–7.83 (m, 2H, ArH).

¹³C-NMR (100 MHz, CDCl₃): 17.7, 18.7, 19.8, 20.4 (CH₃); 33.7, 35.8 (CH); 69.6 (CH₂O); 70.9 (CHN); 88.0 (qC); 127–131 (aromatic C).

Example B6
Preparation of

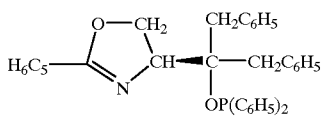

(B6)

Preparation is carried out analogously to Example B1 using compound A5.

Example B7
Preparation of

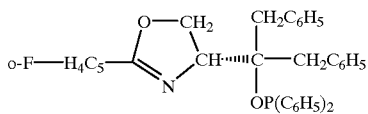

(B7)

Preparation is carried out analogously to Example B1 using compound A7. Column chromatography (15×2 cm, pentane/diethyl ether 10:1) yields 95 mg (27%) of a solid.

¹H-NMR (200 MHz, CD₂Cl₂): 3.19 (d, J=14.1, 1H, CH₂); 3.28 (ddd, J=14.1/2.3/1.2, 2H CH₂); 3.69–3.90 (m, 2H, CH₂, CHN); 4.47 (ddd, J=12.1/ 7.9/1.7, 2H, CH₂O); 7.13–7.65 (M, 23H, ArH); 7.93–8.00 (m, 2H, ArH).

¹³C-NMR (50 MHz, CD₂Cl₂): 42.9, 43.0, 43.5, 43.8 (CH₂); 68.6 (CH₂O); 72.0 (d, $J_{CP}$=2, qC); 85.6 (d, $J_{CP}$=8, CHN); 116–133 (arom, C); 137.6 (d, $J_{CP}$=40, ArP); 144.1 (d, $J_{CP}$=5, ArC); 144.4 (d, J=8, ArC); 161.3 (C=N); 161.7 ($J_{CF}$=258, ArF).

³¹P-NMR (80 MHz, CDCl₃): 83.3.

Example B8
Preparation of

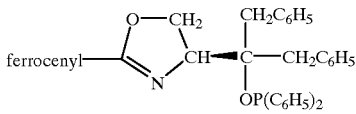

(B8)

Preparation is carried out analogously to Example B1 using compound A8. Column chromatography (15×2 cm, pentane/diethyl ether 10:1) yields 97 mg (40%) of a solid.

¹H-NMR (500 MHz, CD₂Cl₂): 3.10 (d, J=14.0, 1H, CH₂Ar); 3.11 (d, J=13.1, 1H, CH₂Ar); 3.15 (d, J=14.0, 1H, CH₂Ar); 3.38 (d, J=13.1, 1H, CH₂Ar); 3.68 (dd, J=9.9/9.0, 1H, CH₂—O); 3.83 (overlapping dd, J=8.2, 1H, CH₂—O); 4.15 (s, 5H, Cp—H); 4.29 (dd, J=9.9/8.4, 1H, CHN); 4.33 (dt, J=2.4/1.3, 1H, Cp—H); 4.36 (dt, J=2.4/1.3, 1H, Cp—H); 4.64 (overlapping td, J=2.4/1.2, 1H, Cp—H); 4.77 (overlapping td, J=2.4/1.2, 1H, Cp—H); 7.08–7.30 (m, 14H, ArH); 7.39–7.48 (m, 6H, ArH).

¹³C-NMR (125 MHz, CD₂Cl₂): 42.8 (1C, CH₂Ar); 42.9 (1C, CH₂Ar); 68.3 (d, J=3.1, 1C, CH₂O); 69.4 (1C, CpH); 69.4 (1C, CpH); 69.8 (5C, CpH); 70.3 (1C, CpH); 70.5 (1C, CpH); 71.4 (1C, CpC); 71.9 (d, J=4.0, 1C, CHN); 84.8 (d, J=7.2, 1C, Cq); 126.8 (2C, BnH); 128.3 (2C, BnH); 128.3 (2C, BnH); 128.3 (d, $J_{C-P}$=5, 2C, ArH); 128.4 (d, $J_{C-P}$=6, 2C, ArH); 128.9 (1C, ArH); 129.1 (1C, ArH); 130.1 (d, $J_{C-P}$=23, 2C, ArH); 130.3 (d, $J_{C-P}$=22, 2C, ArH); 131.7, 131.7 (4C, BnH); 137.2, 137.7 (1C, BnC); 144.3 (d, J=16, 1C, ArC); 144.4 (d, J=18, 1C, ArC); 166.4 (1C, C=N).

³¹P-NMR (160 MHz, CDCl₃): 85.92 (s, OPAr₂).

Example B9
Preparation of

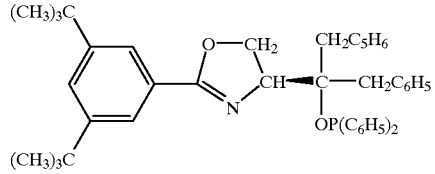

(B9)

Preparation is carried out analogously to Example B1 using compound A9. Column chromatography (15×1 cm, pentane/diethyl ether 20:1) yields 77 mg (78%) of a colourless solid.

¹H-NMR (400 MHz, CD₂Cl₂): 1.37 (s, 18H, H₃CC); 3.12–3.22 (m, 3H, CH₂Ar); 3.62 (d, J=12.9, 1H, ArH); 3.76 (dd, J=10.2/9.0, 1H CH₂O); 3.85 (overlapping m, 1H, CHN); 4.48 (ddd, J=10.2/7.9/1.1, 1H, CH₂O); 7.04–7.21 (m, 8H, ArH); 7.25–7.30 (m, 6H, ArH); 7.32–7.39 (m, 2H, ArH); 7.47–7.51 (m, 2H, ArH); 7.54–7.55 (m, 2H, ArH); 7.60 (t, J=1.8, 1H, ArH); 7.78 (d, J=1.8, 2H, ArH).

¹³C-NMR (100 MHz, CD₂Cl₂): 31.5 (9C, CH₃); 35.1 (2C, qC); 42.3 (1C, CH₂Ar); 43.2 (1C, CH₂Ar); 68.6 (1C, CH₂O); 72.1 (1C, CHN); 85.3 (1C, qC); 122.9, 125.8, 126.8, 126.8, 127.7, 128.3, 128.4, 128.4, 129.1, 130.0, 130.1, 130.2, 130.4, 131.7 (24C, ArH, Arc).

³¹P-NMR (160 MHz, CD₂Cl₂): 85.1.

Example B10
Preparation of

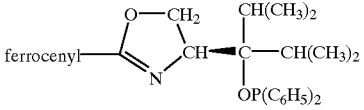

(B10)

Preparation is carried out analogously to Example B1 using compound A10. Column chromatography (15×1 cm, pentane/diethyl ether 10:1) yields 109 mg (46%) of a solid.

¹H-NMR (CD₂Cl₂, 400 MHz): 0.95 (d, J=6.8, 3H, CH₃); 1.05 (d, J=7.1, 3H, CH₃); 1.12 (d, J=7.1, 3H, CH₃); 1.15 (d, J=7.1, 3H, CH₃); 2.56 (dheptet, J=1.5/7.1, 1H, CH); 2.73 (dheptet, J=2.0/7.1, 1H, CH); 4.18 (s, 5H, CpH); 4.27–4.38 (m, 4H, 2*CpH, CH₂O); 4.48 (quintet, J=1.2, 1H, CpH); 4.65–4.70 (m, 1H, CHN); 4.71 (quintet, J=1.2, 1H, CpH); 7.23–7.33 (m, 6H, ArH); 7.48–7.54 (m, 4H, ArH).

¹³C-NMR (CD₂Cl₂, 100 MHz): 18.7 (d, $J_{CP}$=1.5, 1C, CH₃); 19.2 (d, $J_{CP}$=2, 1C, CH₃); 19.3 (d, $J_{CP}$=1.5, 1C, CH₃); 19.4 (d, $J_{CP}$=1.5, 1C, CH₃); 33.7 (d, $J_{CP}$=7, 1C, CH); 34.1

(d, $J_{CP}$6, 1C, CH); 69.1 (1C, CpH); 69.3 (d, $J_{CP}$=3, 1C, CH$_2$O); 69.4 (1C, CpH); 69.7 (5C, CpH); 70.1 (1C, CpH); 70.4 (1C, CpH); 71.2 (d, $J_{CP}$=4, 1C, NCH); 87.9 (d, $J_{CP}$=5, 1C, Cq); 128.4 (d, $J_{CP}$=4, 1C, ArH); 128.5 (d, $J_{CP}$=3, 1C, ArH); 128.8 (1C, ArH); 129.2 (1C, ArH); 129.6 (d, $J_{CP}$=24, 2C, ArH); 130.7 (d, $J_{CP}$=25, 2C, ArH); 144.7 (d, $J_{CP}$=19, 1C, ArP); 145.5 (d, $J_{CP}$=18, 1C, ArP); 165.9 (1C, C=N).

$^{31}$P-NMR (160 MHz, CD$_2$Cl$_2$): 85.2 (d, OPAr$_2$).

Example B11

Preparation of

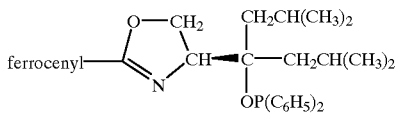
(B11)

Preparation is carried out analogously to Example B1 using compound A11. Column chromatography (15×1 cm, pentane/diethyl ether 6:1) yields 74.6 mg (50%) of a solid.

$^1$H-NMR (400 MHz, CD$_2$Cl$_2$): 0.97 (d, J=6.5, 3H, CH$_3$); 0.98 (d, J=6.3, 3H, CH$_3$); 0.99 (d, J=5.3, 3H, CH$_3$); 1.05 (d, J=6.5, 3H, CH$_3$); 1.67–1.79 (m, 2H, CH$_2$); 1.93–2.03 (m, 2H, CH$_2$); 4.08 (dd, J=8.8/10.1, 1H, CH$_2$O); 4.18 (s, 5H, CpH); 4.24 (dd, J=8.4/7.9, 1H, CH$_2$O); 4.31–4.33 (m, 2H, CpH); 4.53 (dd, J=10.2/7.9, 1H, CHN); 4.61–4.62 (m, 1H, CpH); 4.65–4.66 (m, 1H, CpH); 7.25–7.35 (m, 6H, ArH); 7.49–7.59 (m, 4H, ArH).

$^{13}$C-NMR (100 MHz, CD$_2$Cl$_2$): 23.7 (1C, CH); 23.9 (1C, CH); 25.1 (1C, CH$_3$); 25.3 (1C, CH$_3$); 25.4 (1C, CH$_3$); 25.5 (1C, CH$_3$); 43.9 (d, $J_{CP}$=6, 1C, CH$_2$); 45.0 (d, $J_{CP}$=8, 1C, CH$_2$); 69.0 (d, $J_{CP}$=3, 1C, CH$_2$O); 69.2 (1C, CpH); 69.4 (1C, CpH); 69.7 (1C, CpH); 69.7 (5C, CpH); 70.3 (1C, CpH); 71.4 (1C, CpH); 73.7 (d, $J_{CP}$=5, 1C, CHN); 85.1 (d, $J_{CP}$=7, 1C, qC); 128.4 (d, $J_{CP}$=7, 4C, ArH); 128.9 (1C, ArH); 129.0 (1C, ArH); 130.1 (d, $J_{CP}$=24, 2C, ArH); 130.5 (d, $J_{CP}$=24, 2C, ArH).

$^{31}$P-NMR (160 MHz, CD$_2$Cl$_2$): 85.5 (d, OPAr$_2$).

Example B12

Preparation of

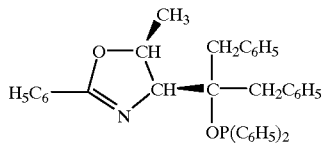
(B12)

Preparation is carried out analogously to Example B1 using compound A12. Column chromatography (ethyl acetate/hexane/triethylamine: 1/15/0.001) yields 310 mg (56% of theory) of a microcrystalline solid.

$^1$H-NMR (400 MHz, CDCl$_3$): δ=1.24 (d, $^3J_{HH}$6.6 Hz, 3H, CH$_3$), 3.11 (d, $^2J_{HH}$=14.4 Hz, 1H, Ph—CH$_2$), 3.33 (d, $^2J_{HH}$=13.4 Hz, 2H, Ph—CH$_2$), 3.72 (d, $^2J_{HH}$=12.9 Hz, 1H, Ph—CH$_2$), 4.34 (d, $^3J_{HH}$=9.6 Hz, 1H, C=N—CH), 4.73 (m, 1H, CH—CH$_3$), 7.05–7.50 (m, 23H, BnH, PhH, PPhH), 8.01 (d, $^3J_{HH}$=7.3 Hz, 2H, PhH).

$^{31}$P{$^1$H}-NMR (161.9 MHz, CDCl$_3$): δ=88.7.

Example B13

Preparation of

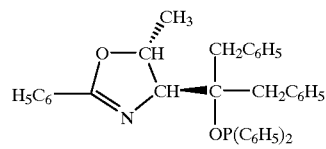
(B13)

Preparation is carried out analogously to Example B1 using compound A13. Column chromatography (ethyl acetate/hexane/triethylamine: 1/15/0.001) yields 270 mg (41% of theory) of a microcrystalline solid.

$^1$H-NMR (400 MHz, CDCl$_3$): δ=1.01 (d, $^3J_{HH}$=6.0 Hz, 3H, CH$_3$), 3.08 (d, $^2J_{HH}$=14.2 Hz, 1H, Ph—CH$_2$), 3.14 (dd, $^4J_{HP}$=2.8 Hz, $^2J_{HH}$=12.9 Hz, 1H, Ph—CH$_2$), 3.18 (d, $^2J_{HH}$=14.2 Hz, 1H, Ph—CH$_2$), 3.51 (d, $^2J_{HH}$=12.9 Hz, 1H, Ph—CH$_2$), 4.00 (d, $^3J_{HH}$=4.8 Hz, 1H, C=N—CH), 4.69 (m, 1H, CH—CH$_3$), 7.02–7.55 (m, 23H, BnH, PhH, PPhH), 7.95 (d, $^3J_{HH}$=7.3 Hz, 2H, PhH).

$^{31}$P{$^1$H}-NMR (161.9 MHz, CDCl$_3$): δ=85.3.

Example B14

Preparation of

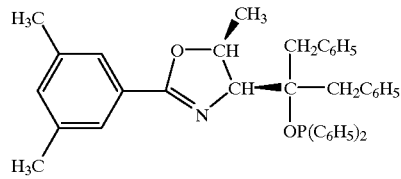
(B14)

Preparation is carried out analogously to Example B1 using compound A14. Column chromatography (ethyl ether/pentane: 1/25) yields 404 mg (53% of theory) of a microcrystalline solid.

$^1$H-NMR (400 MHz, CDCl$_3$): δ=1.26 (d, $^3J_{HH}$=6.6 Hz, 3H, CH$_3$), 2.34 (s, 6H, PhCh$_3$), 3.10 (d, $^2J_{HH}$=14.1 Hz, 1H, Ph—CH$_2$), 3.33 (bd, 2H, Ph—CH$_2$), 3.67 (d, $^2J_{HH}$=12.9 Hz, 1H, Ph—CH$_2$), 4.35 (d, $^3J_{HH}$=9.3 Hz, 1H, C=N—CH), 4.71 (m, 1H, CH—CH$_3$), 7.10–7.50 (m, 21H, BnH, PhH, PPhH), 7.61 (s, 2H, PhH).

$^{31}$P{$^1$H}-NMR (161.9 MHz, CDCl$_3$): δ=88.6.

Example B15

Preparation of

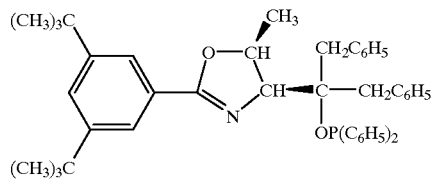
(B15)

Preparation is carried out analogously to Example B1 using compound A15. Column chromatography (ethyl ether/pentane: 1/25) yields 318 mg (51% of theory) of a microcrystalline solid.

$^1$H-NMR (400 MHz, CDCl$_3$): δ=1.33 (d, $^3J_{HH}$=6.3 Hz, 3H, CH$_3$), 1.39 (s, 18H, C(CH$_3$)$_3$), 3.11 (d, $^2J_{HH}$=14.2 Hz, 1H, Ph—CH$_2$), 3.31 (d, $^3J_{HH}$=13.4, 1H, Ph—CH$_2$), 3.40 (d, $^2J_{HH}$=14.6, 1H, Ph—CH$_2$) 3.63 (d, $^2J_{HH}$=12.9 Hz, 1H, Ph—CH$_2$), 4.33 (d, $^3J_{HH}$=9.1 Hz, 1H, C=N—CH), 4.71 (m, 1H, CH—CH$_3$), 7.05–7.51 (m, 20H, BnH, PPhH), 7.57 (s, 1H, PhH), 7.86 (s, 2H, PhH).

$^{31}$P{$^1$H}-NMR (161.9 MHz, CDCl$_3$): δ=88.1.

Example B16

Preparation of

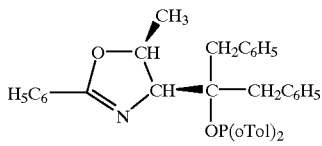
(B16)

Preparation is carried out analogously to Example B1 using compound A12 and chloro-di-ortho-tolyl-phosphine. Column chromatography (ethyl acetate/hexane/triethylamine: 1/15/0.001) yields 160 mg (51% of theory) of a microcrystalline solid.

$^1$H-NMR (400 MHz, CDCl$_3$): δ=1.00 (d, $^3J_{HH}$=6.6 Hz, 3H, CH$_3$), 2.20 (s, 3H, Ph—CH$_3$), (s, 3H, PhCH$_3$), 3.16 (d, $^2J_{HH}$=14.2 Hz, 1H, Ph—CH$_2$), 3.24 (d, $^2J_{HH}$=14.2 Hz, 1H, Ph—CH$_2$), 3.35 (dd, $^4J_{PH}$=2.5 Hz, $^3J_{HH}$=13.1 Hz, 1H, Ph—CH$_2$), 3.79 (d, $^2J_{HH}$=12.9 Hz, 1H, Ph—CH$_2$), 4.41 (d, $^3J_{HH}$=9.1 Hz, 1H, C=N—CH), 4.62 (m, 1H, CH—CH$_3$), 6.95–7.28 (m, 16H, ArH), 7.41–7.52 (m, 5H, ArH), 7.71 (m, 1H, ArH), 8.03 (m, 2H, ArH).

$^{31}$P{$^1$H}-NMR (161.9 MHz, CDCl$_3$): δ=70.7.

Example B17

Preparation of

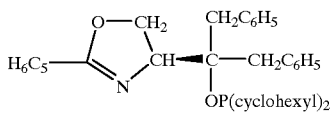
(B17)

Preparation is carried out analogously to Example B1 using compound A6 and chloro-dicyclohexylphosphine. Column chromatography (15×2 cm, hexane/ethyl acetate 10:1) yields 512 mg (52%) of a solid.

$^1$H-NMR (400 MHz, CDCl$_3$): δ=0.92–2.05 (complex m, 22H, CH and CH$_2$ cyclohexyl), 2.87 (d, $^2J_{HH}$=13.9 Hz, 1H, Ph—CH$_2$), 2.95 (d, $^2J_{HH}$=12.6 Hz, 1H, Ph—CH$_2$), 3.04 (d, $^2J_{HH}$13.9 Hz, 1H, Ph—CH$_2$), 3.74–3.88 (m, 2H, O—CH$_2$ and Ph—CH$_2$), 4.00 (d, $^3J_{HH}$=6.8 Hz, 1H, C=N—CH), 4.31 (m, 1H, O—CH$_2$), 7.18–7.34 (m, 8H, ArH), 7.39–7.52 (m, 3H, ArH), 7.63 (m, 2H, ArH), 7.94 (m, 2H, ArH).

$^{31}$P{$^1$H}-NMR (161.9 MHz, CDCl$_3$): δ=122.3.

Example B18

Preparation of

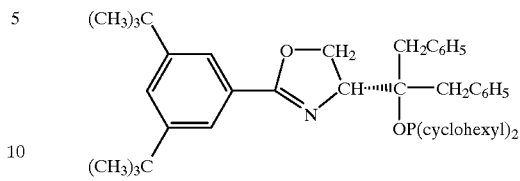
(B18)

Preparation is carried out analogously to Example B1 using compound A9 (starting from D-serine methyl ester) and chlorodicyclohexylphosphine. Column chromatography (15×2 cm, hexane/ethyl acetate 10:1) yields 730 mg (50%) of a solid.

$^1$H-NMR (400 MHz, CDCl$_3$): δ=0.71–2.20 (complex m, 40H, CH and CH$_2$ cyclohexyl, tert-butyl CH$_3$), 2.71–3.02 (m, 4H, PhCH$_2$), 4.00 (d, $J_{HH}$=11.9 Hz, 1H, O—CH$_2$), 4.25 (m, 1H, C=N—CH), 4.73 (d, $J_{HH}$=8.1 Hz, 1H, O—CH$_2$), 6.91–7.42 (m, 10H, ArH), 7.42–7.64 (m, 2H, ArH), 7.81 (sb, 1H, ArH)

$^{31}$P{$^1$H}-NMR (161.9 MHz, CDCl$_3$): δ121.7.

C) PREPARATION OF CATALYSTS

The catalysts prepared according to Examples C1–C18 correspond to formula (COD) Ir L)$^+$tetrakis(3,5-bistrifluoromethylphenyl)borate, wherein L is a ligand according to Examples B1 to B18 and COD is cyclooctadiene. Sodium tetrakis(3,5-bistrifluoromethylphenyl)borate is abbreviated to NaBARF hereinbelow.

Example C1

Ir Catalyst C1 with Ligand B1

57 mg (0.097 mmol) of compound B1 are dissolved in 5 ml of dichloromethane. After the addition of 34.7 mg (0.051 mmol) of [CODIrCl]$_2$, the mixture is heated at reflux and allowed to react until a solution has been formed and the reaction is complete. Then, with vigorous stirring, 91 mg (0.1 mmol) of NaBARF and 3 ml of water are added. After column chromatography (15×2 cm, pentane/diethyl ether 10:1), 450 mg (26% of theory) of a yellowish solid are obtained.

$^1$H-NMR (400 MHz, CDCl$_3$): −0.16 (d, J=6.6, 3H, CH$_3$); 0.50 (d, J=6.3, 3H, CH$_3$); 0.98–1.13 (m, 2H, CH$_2$); 0.99 (d, J=6.6, 3H, CH$_3$); 1.08 (d, J=6.8, 3H, CH$_3$); 1.25–1.50 (m, 4H, CH, CH$_2$, CH$_2$COD); 1.60–1.80 (m, 2H, CH$_2$COD); 1.90 (dd, J=15.4/3.9, 1H, CH$_2$); 2.15–2.20 (m, 2H, CH, CH$_2$, CH$_2$COD); 2.25–2.40 (m, 2H, CH$_2$COD, CHCOD); 2.45–2.52 (m, 2H, CH$_2$COD); 3.25 (m, 1H, CHCOD); 4.07 (m, 1H, CHCOD); 4.58 (dd, J=10.1/3.9, 1H, CH$_2$O); 4.78 (overlapping dd, J=10.1/9.8, 1H, CHN); 4.79–4.87 (mbr, 1H, CHCOD); 5.33 (dd, J=9.8/3.9, 1H, CH$_2$O); 7.18–7.24 (m, 2H, ArH); 7.40–7.50 (m, 3H, ArH); 7.51 (sbr, 4H, BARF-H); 7.58–7.64 (m, 2H, ArH); 7.66–7.72 (m, 1H, ArH); 7.78 (d, J=1.8, 2H, PhH); 7.83 (t, J=1.8, PhH); 8.15–8.23 (m, 2H, ArH).

$^{13}$C-NMR (100 MHz, CDCl$_3$): 22.7 (CH$_3$); 23.3 (2C, CH$_3$); 24.6 (CH$_2$COD); 25.0 (CH); 2.51 (CH); 26.1 (CH$_3$); 26.3 (CH$_2$COD); 31.6 (6C, CH$_3$); 35.6 (qC); 36.5 (CH$_2$); 46.5 (CH$_2$); 62.0 (CHCOD); 68.5 (CHCOD); 70.1 (CH$_2$O); 72.2 (d, $J_{CP}$=5, CHN); 77.6 (CHCOD); 89.9 (d, $J_{CP}$=6, qC); 103.7 (CHCOD); 117.8 (m, 4C, BARF); 123–134 (aromatic C); 135.2 (m, 8C, BARF); 161 (q, $J_{CB}$=49, ArB); 174.9 (C=N).

$^{31}$P—NMR (160 MHz, CDCl$_3$): 92.2.

Example C2
Ir Catalyst C2 with Ligand B2

Preparation is carried out analogously to Example C1. Yield: 100 mg (39% of theory) of an orange solid.

$^1$H-NMR (400 MHz, CDCl$_3$): −0.17 (d, J=6.82, 3H, CH$_3$); 0.76 (d, J=6.32, 3H, CH$_3$); 0.98–1.05 (m, 1H, CH$_2$); 0.99 (d, J=6.57, 3H, CH$_3$); 1.08–1.15 (m, 1H, CH$_2$); 1.12 (d,=6.57, 3H, CH$_3$); 1.20–1.30 (m, 1H, CH$_2$COD); 1.40–1.60 (m, 3H, CH, CH$_2$, CH$_2$COD); 1.70–1.83 (m, 2H, CH$_2$COD); 1.95 (dd, J=15.4/3.8, 1H, CH$_2$); 2.10–2.20 (m, 2H, CH, CH$_2$COD); 2.28–2.60 (m, 4H, CHCOD, CH$_2$COD); 3.84 (sbr, 1H, CHCOD); 3.94 (mbr, 1H, CHCOD); 4.59 (dd, J=10.1/3.3, 1H, CH$_2$O); 4.71 (overlapping dd, J=10.1/9.3, 1H, CHN); 5.04 (mbr, 1H, CHCOD); 5.22 (dd, J=9.313.3, 1H, CH$_2$O); 7.20–7.25 (m, 2H, ArH); 7.42–7.55 (m, 6H, ArH, Biphen); 7.59 (sbr, 4H, BARF-H); 7.60–7.73 (m, 6H, ArH, Biphen); 7.71 (sbr, 8H, BARF-H); 7.85 (d, J=8.6, 2H, Biphen); 8.03–8.08 (m, 2H, ArH); 8.41 (d, J=8.4, 2H, Biphen).

$^{13}$C-NMR (100 MHz, CDCl$_3$): 22.7 (CH$_3$); 23.5 (2C, CH$_3$); 24.8 (CH$_2$COD); 25.0 (CH); 2.53 (CH$_3$); 26.0 (CH$_2$COD); 29.3 (CH); 32.2 (CH$_2$COD); 36.7 (d, CH$_2$); 41.6 (CH$_2$COD); 46.5 (d, J$_{CP}$=7, CH$_2$); 65.0 (CHCOD); 69.5 (CHCOD); 70.4 (CH$_2$O); 71.6 (CHCOD); 77.6 (qC); 90.2 (d, J$_{CP}$=7, CHN); 103.5 (d, J$_{CP}$=11, CHCOD); 117.8 (m, 4C, BARF); 120.8–136 (aromatic C); 135.2 (m, 8C, BARF); 138.8 (ArP); 149.1 (ArP); 162.8 (q, J$_{CB}$=49, ArB); 172.4 (C=N).

$^{31}$P-NMR (160 MHz, CDCl$_3$): 93.8.

Example C3
Ir Catalyst C3 with Ligand B3

Preparation is carried out analogously to Example C1. Yield: 98 mg (28% of theory) of an orange solid.

$^1$H-NMR (400 MHz, CDCl$_3$): 0.00 (d, J=6.6, 3H, CH$_3$); 0.82 (d, J=6.3, 3H, CH$_3$); 1.00 (d, J=6.8, 3H, CH$_3$); 1.09 (d, J=6.8, 3H, CH$_3$); 1.18–1.43 (m, 4H, CH$_2$, CH$_2$COD); 1.49–1.68 (m, 3H, CH$_2$, CH, CH$_2$COD); 1.71–1.83 (m, 1H, CH$_2$COD); 1.93–2.06 (m, 2H, CH$_2$, Ch$_2$COD); 2.10–2.33 (m, 4H, CH, CH$_2$COD); 2.41 (mbr, 1H, CHCOD); 3.30 (mbr, 1H, CHCOD); 3.39 (mbr, 1H, CHCOD); 4.72–4.80 (mbr, 1H, CHCOD); 4.74 (dd, J=10.1/4.0, 1H, CH$_2$O); 5.02 (overlapping dd, J=10.1/9.8, 1H, CHN); 5.27 (dd, J=9.8/4.0, 1H, CH$_2$O); 7.25–7.29 (m, 3H, ArH); 7.42–7.48 (m, 3H, ArH); 7.51 (sbr, 4H, BARF-H); 7.62–7.72 (m, 7H, ArH); 7.72 (sbr, 8H, BARF-H); 7.97–8.03 (m, 2H, ArH); 8.10–8.18 (m, 2H, ArH); 8.21–8.25 (m, 2H, ArH).

$^{13}$C-NMR (100 MHz, CDCl$_3$): 22.8 (CH); 23.4 (CH$_3$); 24.9 (CH); 25.0 (CH$_3$); 25.1 (CH$_3$); 26.1 (CH$_3$); 26.5 (CH$_2$COD); 29.5 (CH$_2$COD); 31.1 (CH$_2$COD); 35.5 (CH$_2$COD); 42.3 (CH$_2$); 46.6 (d, J=6, CH$_2$); 63.0 (CHCOD); 68.2 (CH$_2$O); 71.2 (d, J=5, qC); 71.3 (CHCOD); 90.1 (d, J=7, CHN); 97.8 (d, J=13, CHCOD); 102.7 (d, J=12, CHCOD); 117.8 (m, 4C, BARF); 120.9–137.2 (arom, C); 135.2 (m, 8C, BARF); 162.1 (q, J$_{CB}$=49, ArB); 175.1 (C=N).

$^{31}$P-NMR (160 MHz, CDCl$_3$): 92.4.

Example C4
Ir Catalyst C4 with Ligand B4

Preparation is carried out analogously to Example C1. Column chromatography (15×2 cm, dichloromethane) yields 339 mg (78%) of solid.

$^1$H-NMR (400 MHz, CD$_2$Cl$_2$): 1.32–1.43 (m, 1H, CH$_2$COD); 1.57 (s, 9H, CH$_3$); 1.60–1.77 (m, 2H, CH$_2$COD); 2.07–2.29 (m, 3H, CH$_2$COD); 2.40–2.46 (m, 1H, CH$_2$COD); 2.49–2.57 (m, 1H, CH$_2$COD); 2.58 (d, J=15.4, 1H, CH$_2$Ar); 2.77 (dd, J=15.2/5.1, 1H, CH$_2$Ar); 2.82 (d, J=15.2, 1H, CH$_2$Ar); 3.15 (d, J=14.6, 1H, CH$_2$Ar); 3.88 (mbr, 1H, CHCOD); 4.36–4.43 (m, 1H, CHCOD); 4.64 (overlapping dd, J=9.6/10.1, 1H, CHN); 4.76 (dd, J=10.4/3.1, 1H, CH$_2$O); 5.12 (dd, J=9.3/3.1, 1H, CH$_2$O); 5.06–5.13 (m, 1H, CHCOD); 5.33 (m, 1H, CHCOD); 6.97–7.02 (m, 4H, ArH); 7.10–7.13 (m, 2H, ArH); 7.22–7.26 (m, 3H, ArH); 7.37–7.42 (m, 2H, ArH); 7.42–7.52 (m, 4H, ArH); 7.57 (sbr, 4H, BARF-H); 7.58–7.62 (m, 2H, ArH); 7.66–7.71 (m, 1H, ArH); 7.74 (sbr, 8H, BARF-H); 8.00–8.06 (m, 2H, ArH).

$^{13}$C-NMR (100 MHz, CDCl$_3$): 25.4 (CH$_2$COD); 28.2 (CH$_2$COD); 29.3 (3C, CH$_3$); 33.7 (CH$_2$COD); 34.9 (qC); 37.3 (d, J$_{CP}$=3, CH$_2$Ar); 39.3 (CH$_2$COD); 44.1 (d, J$_{CP}$=6, CH$_2$AR); 65.9 (CHCOD); 68.8 (CHCOD); 69.8 (CH$_2$O); 73.2 (d, J$_{CP}$=4.6, CHN); 88.1 (d, J$_{CP}$=7.6, qC); 91.4 (d, J$_{CP}$=15.3, CHCOD); 100.9 (d, J$_{CP}$=10.7, CHCOD); 117.8 (m, 4C, BARF-H); 123.6–135.7 (ArH, ArC, ArP, CF$_3$); 162.0 (q, J$_{CB}$=49, ArB); 184.7 (C=N).

$^{31}$P-NMR (160 MHz, CDCl$_3$): 99.1.

Example C5
Ir Catalyst C5 with Ligand B5

Preparation is carried out analogously to Example C1. Column chromatography (15×1 cm, diethyl ether/dichloromethane 5:1) yields 109 mg (47%) of red solid.

$^1$H-NMR (400 MHz, CDCl$_3$): 0.62 (d, J=6.8, 3H, CH$_3$); 0.91 (d, J=6.8, 3H, CH$_3$); 0.97 (d, J=7.1, 3H, CH$_3$); 1.17 (d, J=6.6, 3H, CH$_3$); 1.59–1.69 (m, 2H, CH$_2$—COD); 1.73–1.81 (m, 1H, CH$_2$—COD); 1.88–1.97 (m, 1H, CH$_2$—COD); 2.00–2.05 (m, 1H, CH$_2$—COD); 2.16–2.47 (m, 5H, 2 CH(CH$_3$), 3 CH$_2$—COD); 2.82 (m, 1H, CH—COD); 3.81 (m, 1H, CH—COD); 3.90 (m, 1H, CH—COD); 4.67–4.75 (m, 2H, CH$_2$O); 4.80 (m, 1H, CH—COD); 5.18 (dd, J=6.0/10.1, CHN); 7.34–7.40 (m, 2H, ArH); 7.51 (sbr, 4H, BarfH); 7.44–7.59 (m, 8H, ArH); 7.71 (sbr, 9H, 8 BarfH, ArH); 7.85–7.90 (m, 2H, ArH); 8.21 (d, J=7.3, 2H, ArH).

$^{13}$C-NMR (100 MHz, CDCl$_3$): 18.8, 18.8, 18.9, 19.4 (CH$_3$); 26.9, 30.5 (CH$_2$COD); 31.3, 34.1 (CH(CH$_3$); 34.8, 35.5 (CH$_2$COD); 64.6 (CHCOD); 67.5 (CH$_2$O); 70.4 (CHCOD); 70.9 (d, J$_{CP}$=6, CHN); 93.3 (d, J$_{CP}$=8, qC); 95.9 (d, J$_{CP}$=13, CHCOD); 101.7 (d, J$_{CP}$=12, CHCOD); 117.8 (m, 4C, ArH); 123.5–137.2 (arom, C); 135.1 (br, 8C, ArBarf); 162.1 (q with appearance of t, J$_{CB}$=49, ArB); 174.1 (C=N).

$^{31}$P—NMR (160 MHz, CDCl$_3$): 94.02 (OPAr$_2$).

Example C6
Ir Catalyst C6 with Ligand B6

Title compound B6 is prepared analogously to Example C1.

Example C7
Ir Catalyst C7 with Ligand B7

Preparation is carried out analogously to Example C1. Column chromatography (15×1 cm, dichloromethane) yields 207 mg (57% of theory) of orange solid.

$^1$H-NMR (300 MHz, CDCl$_3$): 1.14–1.30 (m, 2H, CH$_2$COD); 1.31–1.65 (m, 2H, CH$_2$COD); 1.90–2.35 (m, 5H, CHCOD, CH$_2$COD; 2.73 (d, J=14.6, 1H, CH$_2$); 2.76 (dd, J=14.7/5.6 1H, CH$_2$); 2.94 (d, J=18.1, 1H, CH$_2$); 2.99 (d, J=17.9, 1H, CH$_2$); 3.17 (m, 1H, CHCOD); 3.72 (m, 1H, CHCOD); 4.50–4.60 (m, 1H, CH$_2$O); 4.63–4.70 (m, 1H, CHCOD); 4.78–4.88 (m, 2H, CH$_2$O, CHN); 6.67–6.69 (m, 2H, ArH); 6.88–7.15 (m, 7H, ArH); 7.28–7.41 (m, 8H, ArH); 7.43 (sbr, 4H, BARF-H); 7.58–7.73 (m, 2H, ArH); 7.64 (sbr, 8H, BARF-H); 8.05–8.15 (m, 2H, ArH).

$^{13}$C-NMR (75 MHz, CDCl$_3$): 26.5, 29.1, 32.4, 35.6 (CH$_2$COD); 41.8, 44.4 (CH$_2$); 63.3 (CHCOD); 68.2 (qC);

70.2 (CHCOD); 77.6 (qC); 88.6 (CHN); 95.2, 102.2 (CHCOD); 117–135 (aromatic C).

Example C8
Ir Catalyst C8 with Ligand B8

Preparation is carried out analogously to Example C1. Column chromatography (15×2 cm, diethyl ether/dichloromethane 6:1) yields 125 mg (98%) of solid.

$^1$H-NMR (600 MHz, CDCl$_3$): 1.31–1.37 (m, 1H, CH$_2$—COD); 1.48–1.63 (m, 2H, CH$_2$COD); 1.80 (m, 1H, CH$_2$—COD); 2.11–2.13 (m, 3H, CH$_2$—COD, CH—COD); 2.30–2.37 (m, 1H, CH$_2$—COD); 2.42–2.49 (m, 1H, CH$_2$—COD); 2.68 (dd, J=15.2/5.3, 1H, CH$_2$Ar); 2.82 (d, J=15.2, 1H, CH$_2$Ar); 2.96 (d, J=15.2, 1H, CH$_2$Ar); 3.16 (d, J=15.2, 1H, CH$_2$Ar); 3.66 (sbr, 1H, CH—COD); 4.15 (s, 5H, CpH); 4.15–4.19 (m, 1H, CH—COD); 4.67 (t, J=9.5, 1H, CH$_2$O); 4.73 (m, 1H, CpH); 4.74 (m, 1H, CH$_2$O); 4.76 (quartet, J=1.2, 1H, CpH); 4.85 (dd, J=9.7/3.1, 1H, CHN); 4.89 (t, J=1.2, 1H, CpH); 4.95 (quartet, J=3.9, 1H, CH—COD); 5.62 (t, J=1.2, 1H, CpH); 6.82 (d, J=7.1, 2H, ArH); 7.01–7.04 (m, 4H, ArH); 7.15–7.21 (m, 3H, ArH); 7.36–7.42 (m, 5H, ArH); 7.51 (mbr, 5H, 4 BARF-H, ArH); 7.71 (mbr, 11H, 8 BARF-H, 3 ArH); 8.21 (dd, J=6.8/11.8, 2H, ArH).

$^{31}$P-NMR (160 MHz, CD$_2$Cl$_2$): 97.2 (s, OPAr$_2$).

Example C9
Ir Catalyst C9 with Ligand B9

Preparation is carried out analogously to Example C1. Column chromatography (15×2 cm, diethyl ether/dichloromethane 6:1) yields 125 mg (98%) of solid.

$^1$H-NMR (400 MHz, CDCl$_3$): 1.25–1.34 (m, 2H, CH$_2$cod); 1.44 (s, 18H, H$_3$CC); 1.60–1.70 (m, 2H, CH$_2$cod); 2.03–2.21 (m, 3H, CH$_2$cod, CHCOD); 2.37–2.51 (m, 2H, CH$_2$cod); 2.72 (d, J=14.6, 1H, CH$_2$Ar); 2.89 (dd, J=14.9/5.5, 1H, CH$_2$Ar); 2.96 (d, J=14.9, 1H, CH$_2$Ar); 3.01 (d, J=14.6, 1H, CH$_2$Ar); 3.26 (mbr, 1H, CHCOD); 4.04–4.11 (m, 1H, CHcod); 4.68 (dd, J=10.1/3.3, 1H, CH$_2$O); 4.75 (mbr, 1H, CHcod); 4.89 (t, J=10.1, 1H, CHN); 5.02 (dd, J=10.1/3.3, 1H, CH$_2$O); 6.68–6.71 (m, 2H, ArH); 6.91–7.19 (m, 7H, ArH); 7.32–7.48 (m, 6H, ArH); 7.50 (s, 4H, BARF-H); 7.66–7.79 (m, 11H, BARF-H, ArH); 7.87–7.89 (m, 3H, ArH); 8.25–8.30 (m, 2H, ArH).

Example C10
Ir Catalyst C10 with Ligand B10

Preparation is carried out analogously to Example C1. Column chromatography (15×2 cm, diethyl ether/dichloromethane 5:1) yields 140 mg (83%) of solid.

$^1$H-NMR (400 MHz, CDCl$_3$): 0.77 (d, J=6.8, 3H, CH$_3$); 0.91 (d, J=7.1, 3H, CH$_3$); 1.15 (d, J=6.6, 3H, CH$_3$); 1.28 (d, J=6.6, 3H, CH$_3$); 1.70–1.84 (m, 2H, CH$_2$cod); 1.96–2.01 (m, 3H, CH$_2$cod, CH); 2.08–2.21(m, 2H, CH$_2$cod); 2.36–2.45 (m, 1H, CH); 2.45–2.54 (m, 2H, CH$_2$cod); 2.97 (m, 1H, CHcod); 3.80 (m, 1H, CHcod); 4.06 (s, 5H, CpH); 4.35 (m, 1H, CHcod); 4.48 (dd, J=10.7/9.9, 1H, CH$_2$O); 4.59 (dd, J=9.7/6.8, 1H, CH$_2$O); 4.67 (m, 1H, CpH); 4.70 (m, 1H, CpH); 4.77 (dd, J=10.7/6.3, 1H, CHN); 4.84 (m, 1h, CHcod); 4.93 (m, 1H, CpH); 5.24 (m, 1H, CpH); 7.29–7.34 (m, 2H, ArH); 7.46–7.48 (m, 3H, ArH); 7.52 (s, 4H, ArH BARF); 7.50–7.59 (m, 3H, ArH); 7.71 (s, 8H, ArH BARF); 7.83–7.88 (m, 2H, ArH).

$^{31}$P—NMR (160 MHz, CDCl$_3$): 93.47 (OPAr$_2$).

Example C11
Ir Catalyst C11 with Ligand B11

Preparation is carried out analogously to Example C1. Column chromatography (15×2 cm, diethyl ether/dichloromethane 5:1) yields 195 mg (87%) of solid.

$^1$H-NMR (400 MHz, CDCl$_3$): −0.09 (d, J=6.8, 3H, CH$_3$); 0.92 (d, J=6.3, 3H, CH$_3$); 0.97 (d, J=6.6, 3H, CH$_3$); 1.09–1.18 (m, 1H, CH$_2$); 1.16 (d, J=6.8, 3H, CH$_3$); 1.38–1.50 (m, 3H, CH$_2$, CH$_2$cod); 1.51–1.70 (m, 2H, CH, CH$_2$cod); 1.70–1.83 (m, 2H, CH$_2$cod); 1.98 (dd, J=15.4/3.8, 1H, CH$_2$); 2.12–2.14 (m, 1H, CH); 2.14–2.24 (m, 1H, CH$_2$cod); 2.24–2.33 (m, 2H, CH$_2$cod, CHcod); 2.33–2.57 (m, 2H, CH$_2$cod); 3.75 (mbr, 1H, CHcod); 4.16 (mbr, 6H, CpH, CHcod); 4.46–4.54 (m, 2H, CH$_2$O, CHN); 4.68 (m, 1H, CpH); 4.72 (m, 1H, CpH); 4.81 (m, 1H, CpH); 4.97 (dd, J=8.8/4.1, 1H, CH$_2$O); 5.00 (mbr, 1H, CHcod); 5.50 (m, 1H, CpH); 7.18–7.22 (m, 2H, ArH); 7.41–7.48 (m, 3H, ArH); 7.52 (sbr, 4H, BARF-H); 7.63–7.73 (m, 3H, ArH); 7.71 (sbr, 8H, BARF-H); 8.05–8.10 (m, 2H, ArH).

$^{31}$P-NMR (160 MHz, CDCl$_3$): 93.56 (s, OPAr$_2$).

Example C12
Ir Catalyst C12 with Ligand B12

Preparation is carried out analogously to Example C1. Column chromatography (15×2 cm, dichloromethane) yields 262 mg (68%) of an orange-coloured solid.

$^1$H-NMR (400 MHz, CDCl$_3$): δ=1.73 (d, $^3J_{HH}$=7.0 Hz, 3H, CH$_3$), 1.75–2.05 (brm, 1H, CH$_2$(COD)), 2.05–2.25 (brm, 1H, CH$_2$(COD)), 2.27–2.33 (brm, 1H, CH$_2$(COD)), 2.95 (dd, $^4J_{PH}$=5.3 Hz, $^3J_{HH}$=14.9 Hz, 1H, Ph—CH$_2$), 3.04 (d, $^2J_{HH}$'14.4 Hz, 1H, Ph—CH$_2$), 3.15–3.38 (brm, 2H, CH(COD)), 3.42 (d, $^2J_{HH}$=14.9 Hz, 1H, Ph—CH$_2$), 4.10–4.35 (brm, 2H, Ph—CH$_2$ and CH(COD)), 4.53 (br, 1H, CH(COD)), 4.75 (d, $^2J_{HH}$=8.1 Hz, 1H, C=N—CH, 5.35 (m, 1H, CH—CH$_3$), 6.93 (m, 2H, ArH), 7.08 (m, 4H, ArH), 7.18 (m, 2H, ArH), 7.23–7.36 (m, 9H, ArH), 7.51 (brs, 4H, ArH(BARF)), 7.52–7.69 (m, 7H, ArH), 7.72 (m, 8H, ArH (BARF)), 7.78 (m, 1H, ArH), 8.39 (brd, 2H, ArH).

$^{31}$P{$^1$H}-NMR (161.9 MHz, CDCl$_3$): δ=93.6.

Example C13
Ir Catalyst C13 with Ligand B13

Preparation is carried out analogously to Example C1. Column chromatography (15×2 cm, dichloromethane) yields 428 mg (73%) of an orange-coloured solid.

$^1$H-NMR (400 MHz, CDCl$_3$): δ=1.35–1.50 (brm, 2H, CH$_2$(COD)), 1.47 (d, $^3J_{HH}$=6.32 Hz, 3H, CH$_3$), 1.55–1.78 (brm, 2H, CH$_2$(COD)), 2.08–2.52 (brm, 5H, CH$_2$ and CH (COD)), 2.52 (d, $^2J_{HH}$=15.2 Hz, 1H, Ph—CH$_2$), 2.89 (m, 2H, Ph—CH$_2$), 3.06 (d, $^2J_{HH}$=15.2 Hz, 1H, Ph—CH$_2$), 3.67 (m, 1H, CH(COD)), 3.82 (brs, 1H, CH(COD)), 4.57 (s, 1H, C=N—CH), 4.93 (brm, 2H, CH—CH$_3$ and CH(COD)), 6.72 (d, $^2J_{HH}$=6.0 Hz, ArH), 7.05–7.18 (m, 7H, ArH), 7.35–7.45 (m, 5H, ArH), 7.51 (brs, 4H, ArH(BARF)), 7.60–7.71 (m, 13H, ArH), 7.72 (m, 8H, ArH(BARF)), 7.78 (m, 1H, ArH), 8.14 (m, 2H, ArH), 8.39 (brd, 2H, ArH).

$^{31}$P{$^1$H}-NMR (161.9 MHz, CDCl$_3$): δ=96.4.

Example C14
Ir Catalyst C14 with Ligand B14

Preparation is carried out analogously to Example C1. Column chromatography (15×2 cm, dichloromethane) yields 229 mg (78%) of an orange-coloured solid.

$^1$H-NMR (500 MHz, CDCl$_3$): δ=1.51–2.10 (brm, 8H, CH$_2$(COD)), 1.77 (d, $^3J_{HH}$=7.0 Hz, 3H, CH$_3$), 2.27–2.36 (brm, 2H, CH(COD)), 2.49 (s, 6H, PhCH$_3$), 2.96 (m, 2H, Ph—CH$_2$), 3.42, (m, 2H, Ph—CH$_2$), 4.42 (br, 2H, CH(COD)), 4.85 (br, 1H, C=N—CH), 5.34 (m, 1H, CH—CH$_3$), 6.82 (brs, 2H, ArH), 6.97 (brs, 2H, ArH), 7.15–7.37 (m, 9H, ArH), 7.44 (brs, 4H, ArH(BARF)), 7.50–7.64 (brm, 3H, ArH), 7.72 (m, 8H, ArH(BARF)), 7.73 (br, 2H, ArH), 8.02 (brs, 2H, ArH).

$^{31}$P{$^1$H}-NMR (161.9 MHz, CDCl$_3$): δ=93.7.

Example C15
Ir Catalyst C15 with Ligand B15

Preparation is carried out analogously to Example C1. Column chromatography (15×2 cm, dichloromethane) yields 578 mg (68%) of an orange-coloured solid.

$^1$H-NMR (500 MHz, CDCl$_3$): δ=1.25–1.32 (br, 2H, CH$_2$ (COD)), 1.43 (s, 18H, C(CH$_3$)$_3$), 1.72–2.33 (br, 7H, CH (1H) and CH$_2$(COD)), 1.87 (d, $^3$J$_{HH}$=7.0 Hz, 3H, CH$_3$), 2.95–3.15 and 3.27–3.38 (brm, total 5H, PH—CH$_2$ and CH(COD)), 4.17 (br, 1H, CH(COD)), 4.68 (br, 1H, CH(COD)), 4.84 (br, 1H, C=N—CH, 5.41 (m, 1H, CH—CH$_3$), 6.93 (br, 2H, ArH), 7.02 (br, 2H, ArH), 7.18 (brm, 2H, ArH), 7.22–7.37 (m, 7H, ArH), 7.51 (brs, 4H, ArH (BARF)), 7.55–7.69 (brm, 6H, ArH), 7.72 (m, 8H, ArH (BARF)), 7.83 (br, 2H, ArH), 7.87 (m, 1H, ArH).

$^{31}$P{$^1$H}-NMR (161.9 MHz, CDCl$_3$): δ=92.1.

Example C16
Ir Catalyst C16 with Ligand B16

Preparation is carried out analogously to Example C1. Column chromatography (15×2 cm, diethyl ether/dichloromethane 4/1) yields 152 mg (73%) of an orange-coloured solid.

$^1$H-NMR (500 MHz, CDCl$_3$): δ=1.24–1.32 (m, $_1$H, CH$_2$ (COD)), 1.41 (d, $^3$J$_{HH}$=7.0 Hz, 3H, CH$_3$), 1.48–1.57 (brm, 2H, CH$_2$(COD)), 1.67–1.76 (brm, 2H, CH$_2$(COD)), 2.05–2.15 (brm, 2H, CH$_2$(COD)), 2.09 (s, 3H, PhCH$_3$), 2.25 (s, 3H, PhCH$_3$), 2.27–2.34 (brm, 1H, CH$_2$(COD)), 2.37–2.53 (m, 2H, CH$_2$(COD) and CH(COD)), 2.75 (m, 2H, Ph—CH$_2$), 3.21 (d, $^2$J$_{HH}$=14.6 Hz, 1H, Ph—CH$_2$), 3.27 (m, 1H, Ph—CH$_2$), 3.47 (m, 1H, CH(COD)), 3.72 (br, 1H, CH(COD)), 4.96 (d, $^3$J$_{HH}$=9 Hz, 1H, C=N—CH), 4.98 (br, 1H, CH(COD)), 5.32 (m, 1H, CH—CH$_3$), 6.55–6.65 (m, 3H, ArH), 7.01–7.08 (m, 5H, ArH), 7.24–7.18 (m, 2H, ArH), 7.32–7.38 (m, 2H, ArH), 7.39–7.42 (m, 1H, ArH), 7.51 (brs, 4H, ArH(BARF)), 7.58–7.68 (brm, 5H, ArH), 7.72 (m, 8H, ArH(BARF)), 7.84 (dt, J=7.5 Hz, J=1.5 Hz, ArH), 8.79 (m, 1H, ArH).

$^{31}$P{$^1$H}-NMR (161.9 MHz, CDCl$_3$): δ=101.1.

Example C17
Ir Catalyst C17 with Ligand B17

Preparation is carried out analogously to Example C1. Column chromatography (15×2 cm, diethyl ether/dichloromethane 4/1) yields 212 mg (42%) of an orange-coloured solid.

$^1$H-NMR (400 MHz, CDCl$_3$): δ=0.88 (m, 1H, CH$_2$cod), 1.27–2.48 (complex m, 29H, CH and CH$_2$ cyclohexyl, CH$_2$cod), 2.59 (m, 1H, CHcod), 2.82 (d, $^2$J$_{HH}$=15.7 Hz, 1H, Ph—CH$_2$), 3.04–3.07 (m, 2H, Ph—CH$_2$), 3.17 (d, $^2$J$_{HH}$=14.4 Hz, 1H, Ph—CH$_2$), 4.22 (dd, $^4$J$_{PH}$=2.3 Hz, $^3$J$_{Hh}$=10.4 Hz, 1H, O—CH$_2$), 4.42 (t, $^3$J$_{HH}$=10.4 Hz, 1H, C=N—CH, 4.72 (m, 1H, O—CH$_2$), 4.83 (mbr, 1H, CHcod), 5.05 (mbr, 1H, CHcod), 7.04 (m, 2H, ArH), 7.23–7.40 (m, 10H, ArH), 7.52 (sbr, 4H, BARH-H), 7.55 (t, J$_{HH}$=7.6 Hz, 1H, ArH), 7.71 (sbr, 8H, BARF-H), 8.40–8.43 (d, J$_{HH}$=7.6 Hz, 2H, ArH).

$^{31}$P{$^1$H}-NMR (161.9 MHz, CDCl$_3$): δ=127.0.

Example C18
Ir Catalyst C18 with Ligand B18

Preparation is carried out analogously to Example C1. Column chromatography (15×2 cm, diethyl ether/dichloromethane 4/1) yields 212 mg (51%) of an orange-coloured solid.

$^1$H-NMR (400 MHz, CDCl$_3$): δ=0.87 (m, 4H, CH$_2$cod), 1.26–1.43 (complex m, 22H, CH and CH$_2$ cyclohexyl, CH$_2$cod, tert-butyl CH$_3$), 1.44–1.87 (m, 14H, CH and CH$_2$ cyclohexyl, CH$_2$cod), 2.08–2.41 (m, 8H, CH and CH$_2$ cyclohexyl, CH$_2$cod), 2.82 (d, $^2$J$_{HH}$=15.2 Hz, 1H, Ph—CH$_2$), 2.93 (t, $^3$J$_{HH}$=7.6 Hz, 1H, Ph—CH$_2$), 3.10 (d, $^2$J$_{HH}$=15.2 Hz, 1H, Ph—CH$_2$), 3.21 (d, $^2$J$_{HH}$=14.7 Hz, 1H, Ph—CH$_2$), 3.40 (mbr, 2H, CHcod), 4.10 (d, J$_{HH}$=10.6 Hz, 1H, O—CH$_2$), 4.40 (t, $^3$J$_{HH}$=9.6 Hz, 1H, C=N—CH0, 4.48 (mbr, 1H, CHcod), 4.90 (m, 2H, O—CH$_2$ and CHcod), 7.02 (m, 2H, ArH), 7.19–7.41 (m, 8H, ArH), 7.52 (sbr, 4H, BARH-H), 7.71 (sbr, 8H, BARF-H), 7.85–7.92 (m, 3H, ArH).

$^{31}$P{$^1$H}-NMR (161.9 MHz, CDCl$_3$): δ=126.3.

D) APPLICATION EXAMPLES

Example D1
Hydrogenation of α-trans-methylstilbene
General Procedure for Hydrogenations 105 mg (0.55 mmol) of α-trans-methylstilbene are dissolved with 3.5 mg (0.002 mmol) of C1 in 0.5 ml of dichloromethane and transferred to a steel autoclave having a glass insert and magnetic stirrer. Then, at RT, a pressure of 50 bar H$_2$ is applied. After 13 hours, the pressure is relieved, the solvent is removed and the residue is taken up in heptane and filtered over silica gel. GC/MS analysis (100° C. für 3 min., 7° C./min to 250° C.) of the solution shows that conversion is complete. The enantiomeric excess is determined by means of chiral HPLC (flow-rate: 0.5 ml/min at 20° C.; stationary phase: Daicel Chiralcel OJ, heptane/isopropanol 99:1) at 97.3% (t$_r$: 13.4 (R), 20.4 (S) min.). The results are given in Table 1.

TABLE 1

| Catalyst | mol % | Duration [h] | Conversion [%] | ee [%] |
|---|---|---|---|---|
| C1 | 0.36 | 5 | 100 | 93 (S) |
| C2 | 0.32 | 24 | 100 | 91.4 (R) |
| C9 | 0.36 | 14 | 100 | 98 (R) |
| C8 | 0.3 | 13 | 100 | 97 (R) |
| C5 | 0.36 | 13 | 100 | 97.3 (R) |
| C12 | 1 | 2 | 100 | 98 (R) |
| C13 | 1 | 2 | 100 | 97 (R) |
| C14 | 1 | 2 | 100 | 99 (R) |
| C15 | 1 | 2 | 100 | 99 (R) |
| C16 | 1 | 2 | 100 | 98 (R) |
| C17 | 1 | 2 | 100 | 95 (R) |
| C18 | 1 | 2 | 100 | 97 (S) |

Example D2a
Hydrogenation of (E)-2-(4-methoxyphenyl)-2-butene

Carried out analogously to D1. Determination of the enantiomeric excess is carried out by means of chiral HPLC [Daicel Chiracel OD-H, heptane/isopropanol 99.99: 0.01) (t$_r$: 13.8 (S), 15.5 (R)].
The results are given in Table 2a.

TABLE 2a

| Catalyst | mol % | Duration [h] | Conversion [%] | ee [%] |
|---|---|---|---|---|
| C1 | 1.2 | 10 | 100 | 83 (S) |
| C4 | 0.6 | 6 | 100 | 65 (R) |
| C8 | 0.14 | 15 | 100 | 96 (R) |
| C5 | 0.2 | 15 | 40 | 45 (R) |
| C11 | 1.3 | 8 | 100 | 95 (R) |
| C10 | 1.1 | 10 | 100 | 93 (R) |
| C9 | 1.0 | 8 | 100 | 95.5 (R) |
| C12 | 1 | 2 | >99 | 99 (R) |

TABLE 2a-continued

| Catalyst | mol % | Duration [h] | Conversion [%] | ee [%] |
|---|---|---|---|---|
| C13 | 1 | 2 | >99 | 98 (R) |
| C14 | 1 | 2 | >99 | 99 (R) |
| C15 | 1 | 2 | >99 | 99 (R) |
| C15 | 0.1 | 2 | >90 | 99.4 (R) |
| C16 | 1 | 2 | >99 | 98 (R) |
| C17 | 1 | 2 | >99 | 95 (R) |
| C18 | 1 | 2 | >99 | 96 (S) |

Example D2b

Hydrogenation of (Z)-2-(4-methoxyphenyl)-2-butene

Carried out analogously to D1. Determination of the enantiomeric excess is carried out by means of chiral HPLC [Daicel Chiracel OD-H, heptane/isopropanol 99.99: 0.01) ($t_r$: 13.8 (S), 15.5 (R)].

The results are given in Table 2b.

TABLE 2b

| Catalyst | mol % | Duration [h] | Conversion [%] | ee [%] |
|---|---|---|---|---|
| C12 | 1 | 2 | >99 | 89 (S) |
| C13 | 1 | 2 | >99 | 88 (S) |
| C14 | 1 | 2 | >99 | 92 (S) |
| C15 | 1 | 2 | >99 | 84 (S) |
| C16 | 1 | 2 | >99 | 83 (S) |

Example D3

Hydrogenation of 2-(4-methoxyphenyl)-1-butene

The hydrogenation is carried out analogously to Example D2.

The results are given in Table 3.

TABLE 3

| Catalyst | mol % | Duration [h] | Conversion [%] | ee [%] | T [° C.] | p [bar] |
|---|---|---|---|---|---|---|
| C1 | 0.6 | 11 | 100 | 39 (R) | 25 | 50 |
| C4 | 0.1 | 14 | 100 | 34 (S) | 25 | 50 |
| C9 | 0.8 | 1 | 100 | 1 (S) | 25 | 50 |
| C8 | 0.09 | 120 | 100 | 67 (S) | 25 | 50 |
| C5 | 0.18 | 120 | 100 | 47 (S) | 25 | 50 |
| C12 | 1 | 0.5 | >99 | 62 (S) | 25 | 50 |
| C12 | 1 | 0.5 | >99 | 89 (S) | 0 | 1 |
| C13 | 1 | 0.5 | >99 | 45 (S) | 25 | 50 |
| C14 | 1 | 0.5 | >99 | 66 (S) | 25 | 50 |
| C14 | 0.1 | 0.5 | >99 | 87 (S) | 0 | 1 |
| C15 | 1 | 0.5 | >99 | 60 (S) | 25 | 50 |
| C15 | 1 | 0.5 | >99 | 84 (S) | 0 | 1 |
| C16 | 1 | 0.5 | >99 | 52 (S) | 25 | 50 |
| C17 | 0.1 | 0.5 | >99 | 84 (S) | 25 | 1 |
| C17 | 0.1 | 0.5 | >99 | 82 (S) | 0 | 1 |
| C18 | 0.1 | 0.5 | >99 | 75 (R) | 25 | 1 |
| C18 | 0.1 | 0.5 | 81 | 85 (R) | 0 | 1 |

Example D4

Hydrogenation of E-phenylbenzimine

Carried out analogously to D1. Determination of the enantiomeric excess is carried out by means of chiral HPLC [Daicel Chiracel OD-H, heptane/isopropanol 99:1) ($t_r$: 22.6 (S), 29.0 (R)].

The results are given in Table 4.

TABLE 4

| Catalyst | mol % | Duration [h] | Conversion [%] | ee [%] |
|---|---|---|---|---|
| C1 | 0.4 | 16 | 100 | 71 (S) |
| C2 | 0.15 | 12 | 82 | 54 (R) |
| C4 | 0.92 | 24 | 100 | 48 (R) |
| C7 | 0.1 | 16 | 100 | 75 (S) |
| C12 | 1 | 4 | 100 | 68 (R) |
| C13 | 1 | 4 | 100 | 53 (R) |
| C14 | 1 | 4 | 100 | 39 (R) |
| C15 | 1 | 4 | 100 | 80 (R) |
| C16 | 1 | 4 | 100 | 80 (R) |

Example D5

Hydrogenation of trans-β-methylcinnamic acid ethyl ester

Carried out analogously to D1. Determination of the enantiomeric excess is carried out by means of chiral HPLC [Daicel Chiracel OB-H, heptane/isopropanol 99.5:0.5) ($t_r$: 24.3 (S), 29.4 (R)].

The results are given in Table 4.

TABLE 4

| Catalyst | mol % | Duration [h] | Conversion [%] | ee [%] |
|---|---|---|---|---|
| C12 | 1 | 2 | >99 | 92 (R) |
| C13 | 1 | 2 | 97 | 86 (R) |
| C14 | 1 | 2 | >99 | 94 (R) |
| C15 | 1 | 2 | 94 | 61 (R) |
| C16 | 1 | 2 | >99 | 70 (R) |
| C17 | 1 | 2 | >99 | 94 (R) |
| C18 | 1 | 2 | >99 | 86 (S) |

What is claimed is:

1. A compound of formula I or Ia,

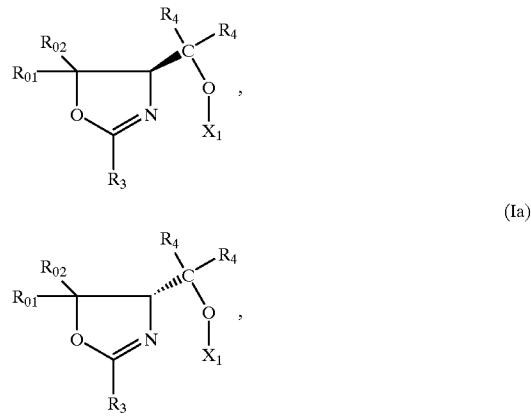

wherein $X_1$ is secondary phosphino;

$R_3$ is hydrogen, a hydrocarbon radical having from 1 to 20 carbon atoms, a heterohydro-carbon radical, bonded via a carbon atom, having from 2 to 20 atoms and at least one hetero atom selected from the group O, S and NR, or ferrocenyl;

R is H or $C_1$–$C_4$alkyl;

each $R_4$ individually or both $R_4$ together are a hydrocarbon radical having from 1 to 20 carbon atoms; and $R_{01}$ and $R_{02}$ are each independently of the other a hydrogen atom or a hydrocarbon radical having from 1 to 20 carbon atoms.

2. A compound according to claim 1, wherein the phosphine groups $X_1$ contain two identical or two different hydrocarbon radicals having from 1 to 22 carbon atoms or the two hydro-carbon radicals form with the P atom a 3- to 8-membered ring.

3. A compound according to claim 2, wherein $X_1$ is the group —$PR_1R_2$ wherein $R_1$ and $R_2$ are each independently of the other a hydrocarbon radical having from 1 to 20 carbon atoms, which is unsubstituted or substituted by halogen, $C_1$–$C_6$alkyl, $C_1$–$C_6$haloalkyl, $C_1$–$C_6$alkoxy, $C_1$–$C_6$haloalkoxy, $(C_6H_5)_3$Si, $(C_1$–$C_{12}$alkyl$)_3$Si or by —$CO_2$—$C_1$–$C_6$alkyl; or wherein $R_1$ and $R_2$ together are dimethylene, trimethylene, tetramethylene or pentamethylene unsubstituted or substituted by $C_1$–$C_4$alkyl or by $C_1$–$C_4$alkoxy.

4. A compound according to claim 3, wherein $R_1$ and $R_2$ are identical or different radicals selected from the group: branched $C_3$–$C_6$alkyl; cyclopentyl or cyclohexyl unsubstituted or substituted by from one to three $C_1$–$C_4$alkyl or $C_1$–$C_4$alkoxy substituents; benzyl unsubstituted or substituted by from one to three $C_1$–$C_4$alkyl or $C_1$–$C_4$alkoxy substituents, and phenyl unsubstituted or substituted by from one to three $C_1$–$C_4$alkyl, $C_1$–$C_4$alkoxy, —$NH_2$, OH, F, Cl, $C_1$–$C_4$fluoroalkyl or $C_1$–$C_4$fluoroalkoxy substituents.

5. A compound according to claim 3, wherein $R_1$ and $R_2$ are identical or different radicals selected from the group: phenyl unsubstituted or substituted by from one to three $C_1$–$C_4$alkyl, $C_1$–$C_4$alkoxy or $C_1$–$C_4$fluoroalkyl substituents.

6. A compound according to claim 1, wherein the hydrocarbon radical $R_3$ contains from 1 to 16 carbon atoms and the heterohydrocarbon radical $R_3$ contains from 1 to 16 atoms and from 1 to 3 hetero atoms selected from the group O, S and NR.

7. A compound according to claim 6, wherein the hydrocarbon radical $R_3$ is $C_1$–$C_{18}$alkyl; $C_3$–$C_{12}$cycloalkyl; or $C_6$–$C_{16}$aryl, and the heterohydrocarbon radical $R_3$ is $C_1$–$C_{18}$heteroalkyl, $C_3$–$C_{12}$heterocycloalkyl or $C_4$–$C_{16}$heteroaryl.

8. A compound according to claim 7, wherein $R_3$ is a hydrocarbon radical selected from the group: branched $C_3$–$C_{12}$alkyl, $C_5$–$C_6$cycloalkyl and $C_5$–$C_{12}$aryl, the cyclic radicals being unsubstituted or substituted by halogen, $C_1$–$C_4$alkyl or by $C_1$–$C_4$alkoxy.

9. A compound according to claim 1, wherein $R_4$ is a hydrocarbon radical selected from the group: branched $C_3$–$C_{12}$alkyl, $C_5$–$C_6$cycloalkyl, $C_6$–$C_{12}$aryl and $C_7$–$C_{12}$aralkyl, the cyclic radicals being unsubstituted or substituted by halogen, $C_1$–$C_4$alkyl, $C_1$–$C_4$haloalkyl or by $C_1$–$C_4$alkoxy.

10. A compound according to claim 1, wherein $R_{01}$ and $R_{02}$ are each independently of the other H, $C_1$–$C_{12}$alkyl, $C_5$–$C_6$cycloalkyl, $C_6$–$C_{12}$aryl or $C_7$–$C_{12}$aralkyl, the cyclic radicals being unsubstituted or substituted by halogen, $C_1$–$C_4$alkyl, $C_1$–$C_4$haloalkyl or by $C_1$–$C_4$alkoxy.

11. A compound according to claim 1, which corresponds to formula Ib or Ic

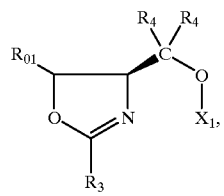

(Ib)

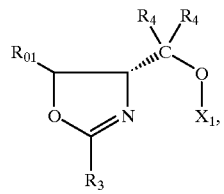

(Ic)

wherein $X_1$ is —$PR_1 R_2$, $R_{01}$ is hydrogen or $C_1$–$C_4$alkyl, $R_1$ and $R_2$ are identical or different and are selected from the group: α-branched $C_3$–$C_6$alkyl; $C_5$–$C_7$cycloalkyl unsubstituted or substituted by from one to three $C_1$–$C_4$alkyl or $C_1$–$C_4$alkoxy substituents; phenyl unsubstituted or substituted by from one to three $C_1$–$C_4$alkyl, $C_1$–$C_4$-alkoxy or $C_1$–$C_4$fluoroalkyl substituents; and dimethylene, trimethylene, tetramethylene or hexamethylene unsubstituted or substituted by $C_1$–$C_4$alkyl or by $C_1$–$C_4$alkoxy;

$R_3$ is a hydrocarbon radical selected from the group: branched $C_3$–$C_{12}$alkyl, $C_5$–$C_6$cycloalkyl, $C_6$–$C_{12}$aryl and ferrocenyl, the cyclic radicals being unsubstituted or substituted by halogen, $C_1$–$C_4$alkyl, $C_1$–$C_4$haloalkyl or by $C_1$–$C_4$alkoxy; and $R_4$ is a hydrocarbon radical selected from the group: branched $C_3$–$C_{12}$alkyl, $C_5$–$C_6$cycloalkyl, $C_6$–$C_{12}$aryl and $C_7$–$C_{12}$aralkyl, the cyclic radicals being unsubstituted or substituted by halogen, $C_1$–$C_4$alkyl or by $C_1$–$C_4$alkoxy.

12. A process for the preparation of a compound of formula I or Ia,

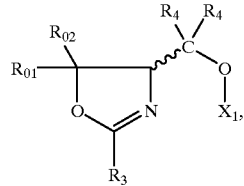

(I and Ia)

wherein $R_{01}$, $R_{02}$, $R_3$, $R_4$ and $X_1$ are as defined above, and ~ denotes the R- or S-form, in which process either a1) a compound of formula II

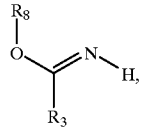

(II)

or a salt thereof, wherein $R_3$ is as defined above and $R_8$ is $C_1$–$C_4$alkyl, is reacted with at least an equivalent amount of a compound of formula III,

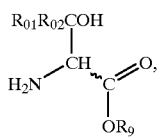 (III)

wherein $R_9$ is $C_1$–$C_4$alkyl, to form a compound of formula IV,

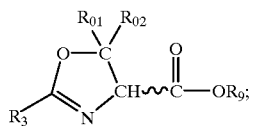 (IV)

a2) the compound of formula IV is reacted with at least 2 equivalents of an organometal compound of formula V or Va $R_4$—$X_2$ (V), $R_4$—$(X_2)_2$ (Va), wherein $R_4$ is as defined above, $X_2$ is an alkali metal or —$Me_1X_3$, $Me_1$ is Mg or Zn, and $X_3$ is Cl, Br or I, to form a compound of formula VI

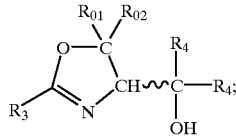 (VI)

and a3) the hydroxyl group in the compound of formula VI is metallated and then reacted with a halophosphine of formula VII, $X_1$—$Y_1$ (VII), wherein $X_1$ is as defined above and $Y_1$ is Cl, Br or I, to form a compound of formula Ia or Ib; or b1) a carboxylic acid of formula VIII $R_3$—COOH (VIII), or a derivative of that carboxylic acid, is reacted with a compound of formula III to form a carboxylic acid amide of formula IX,

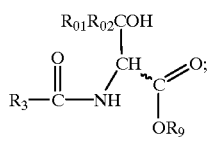 (IX)

b2) the compound of formula IX is reacted with a compound of formula V or Va to form a compound of formula X,

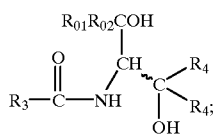 (X)

b3) the compound of formula X is cyclised to form a compound of formula VI; and b4) the hydroxyl group in the compound of formula VI is metallated and then reacted with a halophosphine of formula VII to form a compound of formula Ia or Ib.

* * * * *